United States Patent
Wei et al.

(10) Patent No.: US 8,843,193 B2
(45) Date of Patent: Sep. 23, 2014

(54) TWA MEASURING APPARATUS AND TWA MEASURING METHOD

(71) Applicants: Daming Wei, Funabashi (JP); Nihon Kohden Corporation, Tokyo (JP)

(72) Inventors: Daming Wei, Funabashi (JP); Jiro Suto, Tokyo (JP); Takashi Kaiami, Tokyo (JP); Motoki Sakai, Aizu-Wakamatsu (JP)

(73) Assignees: Wei Daming, Chiba (JP); Nihon Kohden Corporation, Tokyo (JP)

( * ) Notice: Subject to any disclaimer, the term of this patent is extended or adjusted under 35 U.S.C. 154(b) by 0 days.

(21) Appl. No.: 13/784,894

(22) Filed: Mar. 5, 2013

(65) Prior Publication Data

US 2013/0237871 A1    Sep. 12, 2013

(30) Foreign Application Priority Data

Mar. 6, 2012    (JP) ................ 2012-049525

(51) Int. Cl.
*A61B 5/04* (2006.01)
*A61B 5/0452* (2006.01)
*A61B 5/0402* (2006.01)

(52) U.S. Cl.
CPC ........... *A61B 5/0452* (2013.01); *A61B 5/04011* (2013.01); *A61B 5/04012* (2013.01); *A61B 5/04028* (2013.01)
USPC .......................................... 600/509; 600/512

(58) Field of Classification Search
CPC ........................ A61B 5/0452; A61B 5/04011
USPC ................................. 600/509, 512
See application file for complete search history.

(56) References Cited

U.S. PATENT DOCUMENTS

| | | | |
|---|---|---|---|
| 4,802,491 A | 2/1989 | Cohen et al. | |
| 5,935,082 A | 8/1999 | Albrecht et al. | |
| 6,668,189 B2 | 12/2003 | Kaiser et al. | |
| 2007/0260151 A1 | 11/2007 | Clifford | |
| 2008/0015452 A1* | 1/2008 | Ricci et al. | 600/509 |
| 2009/0306526 A1 | 12/2009 | Cuesta Frau et al. | |

FOREIGN PATENT DOCUMENTS

EP    2 412 308 A2    2/2012

OTHER PUBLICATIONS

Extended European Search Report, dated Apr. 16, 2014, issued by the European Patent Office in counterpart European Application No. 13158014.4.
Man, S. et al., "Individually Improved VCG Synthesis," Computers in Cardiology, 2009, IEEE, Sep. 13, 2009, pp. 277-280.
Takahashi, Kunio et al., "Development of Digital Image Surface and its Application to Derived 12-lead ECG," Seventh International Conference on Computer and Information Technology, Oct. 16-19, 2007, pp. 1122-1126.

* cited by examiner

*Primary Examiner* — Nicole F Lavert
(74) *Attorney, Agent, or Firm* — Sughrue Mion, PLLC

(57) ABSTRACT

A TWA measuring apparatus includes: an electrocardiograph controlling section which is configured to produce an electrocardiogram from electrocardiographic signals of a subject; and a TWA measuring section which is configured to select at least two waveforms that contribute to a measurement of TWA, from the electrocardiogram, and which is configured to measure a presence of TWA by using the selected at least two waveforms.

18 Claims, 28 Drawing Sheets

TWA MEASURING APPARATUS AND TWA MEASURING METHOD

CROSS-REFERENCE TO RELATED APPLICATION(S)

This application is based upon and claims the benefit of priority from prior Japanese patent application No. 2012-049525, filed on Mar. 6, 2012, the entire contents of which are incorporated herein by reference.

BACKGROUND

The presently disclosed subject matter relates to a TWA measuring apparatus and TWA measuring method which can measure the presence of TWA (T-Wave Alternans).

TWA appears at onset of illness such as QT prolongation syndrome, variant angina, acute myocardial ischemia, electrolyte abnormality, paroxysmal tachycardia, bradycardia, or pericardial fluid accumulation. TWA is a phenomenon in which the amplitude and polarity of the T wave appearing in an electrocardiogram are alternately changed, and an index effective to predict sudden cardiac death. TWA is not a phenomenon which can be always observed with the naked eye, and therefore its application in clinics is limited.

From the 1980s, consequently, techniques for enabling minute TWA (Microvolt TWA: MTWA) to be measured by a computer have been developed.

Examples of currently proposed techniques for measuring TWA are a measurement technique based on the MMA (Modified Moving Average) method of General Electric (GE) Company, and a measurement technique based on the periodogram of Cambridge Heart (CH), Inc., which are disclosed in U.S. Pat. No. 6,668,189 and U.S. Pat. No. 5,935,082, respectively.

The measurement technique of GE Company is directed to a method of analyzing a time waveform in a time region, and is said to have resistance to noises. However, the technique does not have a long history as a measurement technique, and it is required to watch its clinical effect.

By contrast, the measurement technique of CH Inc. which is a technique in a frequency region has been used from the 1980s, and hence its effectiveness in clinics has been proved. Today, therefore, it is considered that the measurement technique based on the periodogram of CH Inc. is clinically more useful than that based on the MMA method of GE Company.

With respect to the measurement technique based on the periodogram of CH Inc., after its announcement, various techniques for performing new processes, such as a technique of measurement electrodes are added, and still now the added latest techniques have been used.

The technique for measuring TWA based on the periodogram disclosed in U.S. Pat. No. 5,935,082 is based on the assumption that various conditions are satisfied, such as the heart rate must be kept constant in an exercise test, and the heart rate in an abnormal case such as extrasystole must be suppressed to a specified value or smaller.

Depending on the subject, however, there is a case where the heart rate cannot be kept constant in an exercise test. There is a further case where, even when the heart rate can be kept substantially constant, noises may enter in several beats. Moreover, the subject cannot suppress the heart rate in an abnormal case such as extrasystole to a specified value or smaller.

In the technique for measuring TWA disclosed in U.S. Pat. No. 5,935,082, even when measurement of TWA is tried to be performed without satisfying the above conditions, data collection for measuring TWA is not started. Even in the case where data collection is started, when the above conditions become unsatisfied in the middle of the measurement, the data collection is reset.

Furthermore, since the measurement is performed while satisfying the above conditions, the inspection time tends to be prolonged, and hence an extra burden is imposed on the measuring person and the subject. The TWA measurement is not ended unless the above conditions are satisfied. In the case where time is limited, therefore, the TWA measurement cannot be completed.

SUMMARY

The presently disclosed subject matter may provide a TWA measuring apparatus and a TWA measuring method which can reduce the burden on the measuring person and the subject, and which can measure the presence of TWA from an electrocardiogram acquired by any one of various measuring methods.

The TWA measuring apparatus may comprise: an electrocardiograph controlling section which is configured to produce an electrocardiogram from electrocardiographic signals of a subject; and a TWA measuring section which is configured to select at least two waveforms that contribute to a measurement of TWA, from the electrocardiogram, and which is configured to measure a presence of TWA by using the selected at least two waveforms.

The TWA measuring apparatus may further comprise a transformation coefficient storing section which is configured to store a transformation coefficient. The electrocardiogram may be a Frank's vector electrocardiogram, the electrocardiograph controlling section may synthesize the Frank's vector electrocardiogram from the electrocardiographic signals by using the transformation coefficient, and the TWA measuring section may select the at least two waveforms from waveforms of a vector magnitude which is calculated from the Frank's vector electrocardiogram.

The transformation coefficient storing section may include: a personal coefficient database which is configured to store, as the transformation coefficient, a personal coefficient which is specific to the subject and which is acquired from the subject; and a group coefficient database which is configured to store, as the transformation coefficient, a group coefficient which is an average of a plurality of transformation coefficients which are acquired from an unspecified number of persons of a statistically effective population in order to synthesize the Frank's vector electrocardiogram of the subject.

When the personal coefficient acquired from the subject exists in the personal coefficient database, the electrocardiograph controlling section may synthesize the Frank's vector electrocardiogram by using the personal coefficient as the transformation coefficient. When the personal coefficient does not exist in the personal coefficient database, the electrocardiograph controlling section may synthesize the Frank's vector electrocardiogram by using the group coefficient existing in the group coefficient database as the transformation coefficient.

When the personal coefficient of the subject does not exist in the personal coefficient database, the electrocardiograph controlling section may cause a displaying section to display a message for prompting acquisition of the personal coefficient.

The electrocardiograph controlling section may calculate the personal coefficient of the subject from the electrocardiographic signals, and store the calculated personal coefficient in the personal coefficient database.

The electrocardiogram may be a Frank's vector electrocardiogram, the electrocardiograph controlling section may directly produce the Frank's vector electrocardiogram from the electrocardiographic signals, and the TWA measuring section may select the at least two waveforms from waveforms of a vector magnitude which is calculated from the Frank's vector electrocardiogram.

The electrocardiogram may be a scalar electrocardiogram, the electrocardiograph controlling section may synthesize or directly produce the scalar electrocardiogram from the electrocardiographic signals, and the TWA measuring section may select the at least two waveforms from waveforms of the scalar electrocardiogram.

The scalar electrocardiogram may be one of a 12-lead electrocardiogram, a Holter electrocardiogram, an event electrocardiogram, an exercise electrocardiogram, and a monitoring electrocardiogram.

The TWA measuring section may select the at least two waveforms that contribute to the measurement of TWA, from waveforms of a plurality of heart beats.

In a case where an abnormal value is included in the at least two waveforms that contribute to the measurement of TWA, the TWA measuring section may correct the abnormal value.

The TWA measuring method may comprise: producing an electrocardiogram from electrocardiographic signals of a subject; selecting at least two waveforms that contribute to a measurement of TWA, from the electrocardiogram; and measuring a presence of TWA by using the selected at least two waveforms.

The electrocardiogram may be a Frank's vector electrocardiogram, the Frank's vector electrocardiogram may be synthesized from the electrocardiographic signals by using a transformation coefficient, and the at least two waveforms may be selected from waveforms of a vector magnitude which is calculated from the Frank's vector electrocardiogram.

The electrocardiogram may be a Frank's vector electrocardiogram, the Frank's vector electrocardiogram may be directly produced from the electrocardiographic signals, and the at least two waveforms may be selected from waveforms of a vector magnitude which is calculated from the Frank's vector electrocardiogram.

The electrocardiogram may be a scalar electrocardiogram, the scalar electrocardiogram may be synthesized or directly produced from the electrocardiographic signals, and the at least two waveforms may be selected from waveforms of the scalar electrocardiogram.

The scalar electrocardiogram may be one of a 12-lead electrocardiogram, a Holter electrocardiogram, an event electrocardiogram, an exercise electrocardiogram, and a monitoring electrocardiogram.

The at least two waveforms that contribute to the measurement of TWA may be selected from waveforms of a plurality of heart beats.

In a case where an abnormal value is included in the at least two waveforms that contribute to the measurement of TWA, the abnormal value may be corrected.

DETAILED DESCRIPTION OF EXEMPLARY EMBODIMENTS

In the TWA measuring apparatus and the TWA measuring method of the presently disclosed subject matter, the presence of TWA can be measured from an electrocardiogram acquired by any one of various measuring methods.

Hereinafter, embodiments of the TWA measuring electrocardiograph, which is one example of the TWA measuring apparatus, and the TWA measuring method of the presently disclosed subject matter will be described respectively in Embodiment 1 to Embodiment 3.

In Embodiment 1, a Frank's vector electrocardiogram is synthesized from a scalar electrocardiogram such as a 12-lead electrocardiogram, and the presence of TWA is measured from the Frank's vector electrocardiogram. Since a Frank's vector electrocardiogram is synthesized from a scalar electrocardiogram, the measuring person is enabled to measure the presence of TWA simply by attaching measurement electrodes to the subject in the same manner as in acquisition of a scalar electrocardiogram.

Hereinafter, a TWA measuring electrocardiograph and TWA measuring method of Embodiment 1 will be described by exemplifying a case where a 12-lead electrocardiogram is used as a scalar electrocardiogram. Although the case where a 12-lead electrocardiogram is used will be exemplarily described in Embodiment 1, the presently disclosed subject matter can be applied also to the case where an at least 3-lead scalar electrocardiogram including the synthesized lead is used. Examples of an at least 3-lead scalar electrocardiogram are a 12-lead electrocardiogram, a Holter electrocardiogram, an event electrocardiogram, an exercise electrocardiogram, and a monitoring electrocardiogram.

Embodiment 1

In the TWA measuring electrocardiograph and TWA measuring method of Embodiment 1, a 12-lead electrocardiogram is produced from electrocardiographic signals of measurement electrodes. In the TWA measuring electrocardiograph and TWA measuring method of Embodiment 1, as described above, a Frank's vector electrocardiogram can be synthesized from a 12-lead electrocardiogram, and the presence of TWA which is effective in prognostic diagnosis of sudden cardiac death can be measured from the synthesized Frank's vector electrocardiogram.

In the embodiment, the term "patient" is used as a specific example of the subject. However, the patient includes not only the patient who receives a diagnosis in a hospital, but also a user of an institution other than a hospital, such as a medical examination center or clinic which performs health checkup, or a usual house.

(Configuration of TWA Measuring Electrocardiograph)

Figure 1:
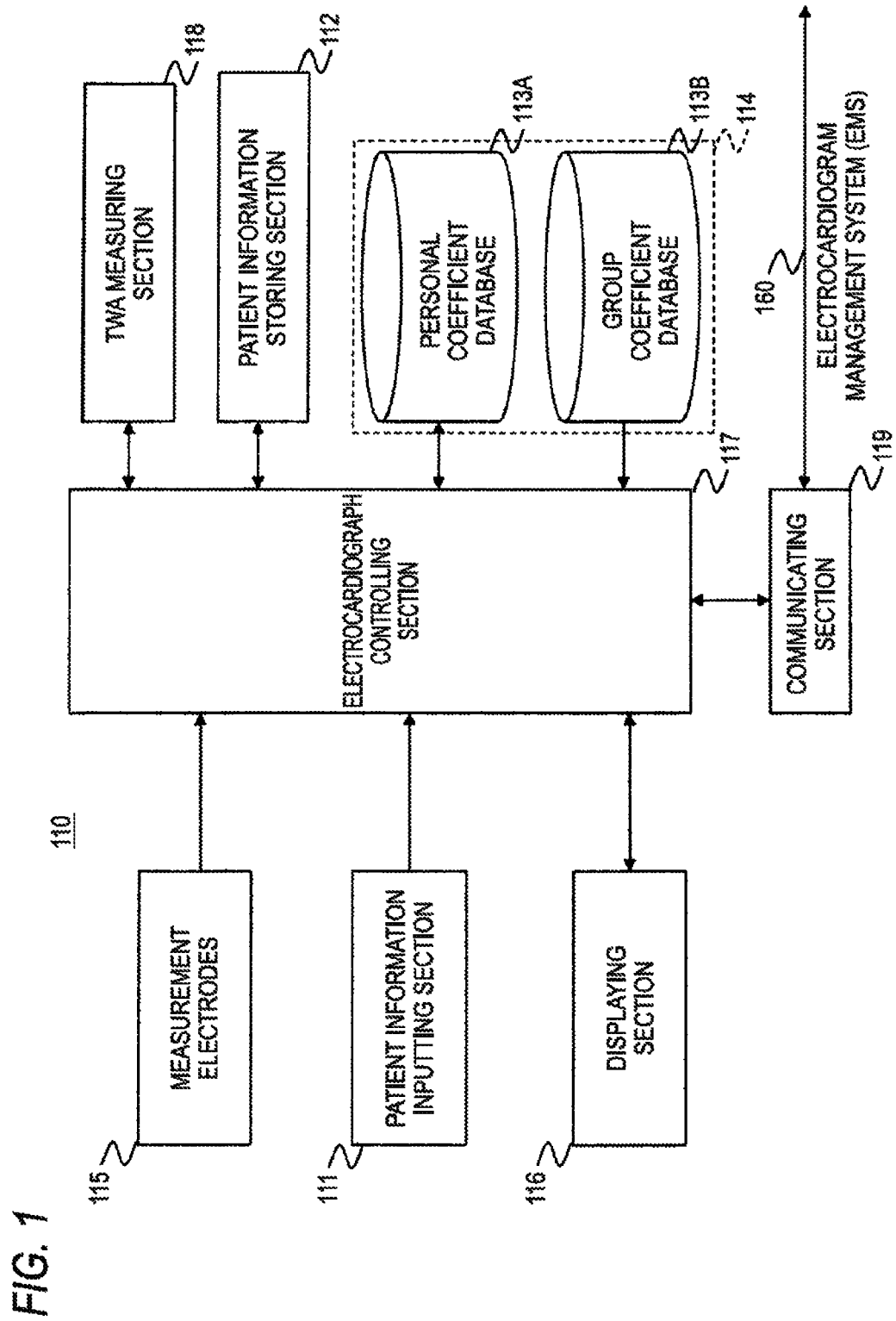
FIG. 1 is a block diagram of a TWA measuring electrocardiograph of Embodiment 1.

First, the configuration of the TWA measuring electrocardiograph of Embodiment 1 will be described. FIG. 1 is a block diagram of the TWA measuring electrocardiograph of Embodiment 1.

The TWA measuring electrocardiograph 110 includes a patient information inputting section 111, a patient information storing section 112, a transformation coefficient storing section 114, measurement electrodes 115, a displaying section 116, an electrocardiograph controlling section 117, a TWA measuring section 118, and a communicating section 119. The transformation coefficient storing section 114 includes a personal coefficient database 113A and a group coefficient database 113B.

The patient information inputting section 111 is used for inputting patient information by means of key operations of the measuring person. Specifically, the patient information contains a patient ID (specific ID and individual ID) (for acquiring a personal coefficient), the name of the patient (for acquiring the personal coefficient), the age of the patient (for acquiring a group coefficient), and the sex of the patient (for acquiring the group coefficient).

The patient information storing section 112 stores the patient information which is input through the patient information inputting section 111. For example, the specific ID "C123" and individual ID "A123" of the patient, the name of the patient, the age of the patient, and the sex of the patient are stored as the patient ID.

The transformation coefficient storing section 114 stores a transformation coefficient for deriving a Frank's vector electrocardiogram from a 12-lead electrocardiogram.

The personal coefficient database 113A constituting the transformation coefficient storing section 114 stores a personal coefficient which is previously acquired from a specific patient, and which is specific to the subject, as the transformation coefficient. The personal coefficient is stored for each patient and in time series. In the above-described case, for example, the specific ID "C123" of the patient, the individual ID "A123" of the patient, and the name of the patient are added as additional information of the personal coefficient, and stored for each patient and in time series.

When a Frank's vector electrocardiogram is to be synthesized, usually, it is sufficient to use one latest personal coefficient. Even so, a plurality of personal coefficients are stored in time series because there is a case where the progress of symptoms or the recovery state can be known by observing a change of the personal coefficient or that of a Frank's vector electrocardiogram which is synthesized by using past personal coefficients and the current personal coefficient.

The group coefficient database 113B constituting the transformation coefficient storing section 114 stores, as a transformation coefficient, a group coefficient which is the average of a plurality of transformation coefficients acquired from an unspecified number of persons of a statistically effective population in order to synthesize a Frank's vector electrocardiogram of the patient. The group coefficient is stored for each sex and age group.

The measurement electrodes 115 are electrodes which are to be attached to the body surface of the patient. The measurement electrodes 115 are used when a 12-lead electrocardiogram is to be produced, or when the personal coefficient which is specific to the patient is to be acquired.

The displaying section 116 displays the patient information which is input through the patient information inputting section 111, and a measurement result of the presence of TWA which is measured by the TWA measuring section 118, on a display device, or prints out them.

The electrocardiograph controlling section 117 produces a 12-lead electrocardiogram from electrocardiographic signals of the measurement electrodes 115, and synthesizes a Frank's vector electrocardiogram from the 12-lead electrocardiogram by using the transformation coefficient of the transformation coefficient storing section 114. When the personal coefficient acquired from the patient exists in the personal coefficient database 113A, the electrocardiograph controlling section 117 synthesizes a Frank's vector electrocardiogram while using the personal coefficient as the transformation coefficient. This is because, when the personal coefficient of the patient is used, the accuracy of the measurement of TWA is improved. By contrast, when the personal coefficient acquired from the patient does not exist in the personal coefficient database 113A, a Frank's vector electrocardiogram is synthesized while using the group coefficient existing in the group coefficient database 113B as the transformation coefficient, in order to enable the measurement of TWA to be performed even when there is no personal coefficient specific to the patient.

When there is no personal coefficient specific to the patient in the personal coefficient database 113A, the electrocardiograph controlling section 117 causes the displaying section 116 to display a message for prompting the acquisition of the personal coefficient of the patient. This is because the promotion of the acquisition of the personal coefficient contributes the improvement of the measurement accuracy. In the case where the personal coefficient specific to the patient is to be acquired, the electrocardiograph controlling section 117 calculates the personal coefficient specific to the patient from electrocardiographic signals of the measurement electrodes 115 attached to the body surface of the patient, and stores the calculated personal coefficient in the personal coefficient database 113A.

In the case where the personal coefficient specific to the patient is to be acquired, in order to produce a 12-lead electrocardiogram, first, the measurement electrodes 115 are attached respectively to measurement portions of the patient which are determined in each measuring method, and a 12-lead electrocardiogram is produced from electrocardiographic signals of the measurement electrodes 115.

Next, the measurement electrodes 115 are attached respectively to measurement portions of the patient which are determined for producing a Frank's vector electrocardiogram, and a Frank's vector electrocardiogram is produced from electrocardiographic signals of the measurement electrodes 115. The portions to which the measurement electrodes 115 are attached for producing a 12-lead electrocardiogram are different from those to which the measurement electrodes 115 are attached for producing a Frank's vector electrocardiogram.

The production of a 12-lead electrocardiogram may be performed separately from that of a Frank's vector electrocardiogram. In Embodiment 1, however, the productions of the electrocardiograms are simultaneously performed in order to improve the working efficiency.

The electrocardiograph controlling section 117 calculates a personal coefficient which is specific to the patient, and which is used for matching the 12-lead electrocardiogram to the Frank's vector electrocardiogram. The electrocardiograph controlling section 117 stores the calculated personal coefficient in the personal coefficient database 113A for each patient and in time series, while adding the specific ID of the patient, the individual ID of the patient, and the name of the patient to the personal coefficient as additional information of the personal coefficient.

The electrocardiograph controlling section 117 generally controls the above-described various operations, and also all operations of the TWA measuring electrocardiograph 110. The electrocardiograph controlling section 117 includes programs for realizing the all operations of the TWA measuring electrocardiograph 110. The operation of the electrocardiograph controlling section 117 will be described later in detail.

The TWA measuring section 118 measures the presence of TWA from the Frank's vector electrocardiogram which is synthesized by the electrocardiograph controlling section 117. In the measurement of the presence of TWA, the TWA measuring section 118 selects waveforms which can contribute to the measurement of the presence of TWA, from a plurality waveforms of the Frank's vector electrocardiogram synthesized by the electrocardiograph controlling section 117, and measures the presence of TWA from the selected waveforms. This is because, when waveforms which can contribute to the measurement of the presence of TWA are selected, the accuracy of the measurement of TWA is improved. The operation of the TWA measuring section 118 will be described later in detail.

The communicating section 119 transmits the personal coefficient of the patient to an electrocardiogram management system (EMS) 140 (see FIG. 12), and conversely receives a personal coefficient of a patient which is requested by the electrocardiograph controlling section 117, from the EMS 140. The transmission/reception of a personal coefficient in the communicating section 119 can be performed through an intra-hospital network 160.

(Operation of TWA Measuring Electrocardiograph)

Next, the operation of the TWA measuring electrocardiograph of Embodiment 1 will be described with reference to the operation flowchart of FIG. 2.

Figure 2:
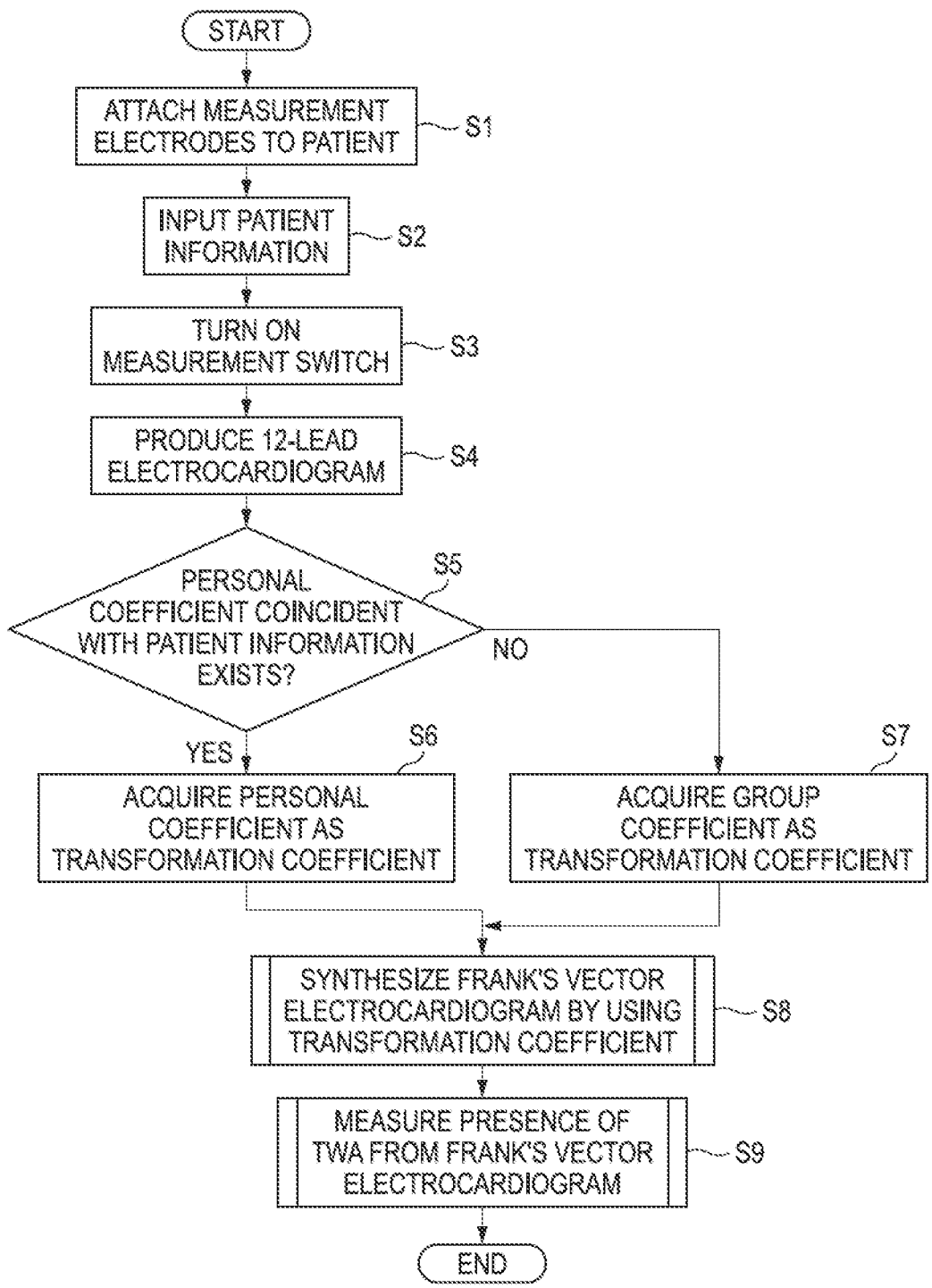
FIG. 2 is an operation flowchart of the TWA measuring electrocardiograph of Embodiment 1.

In the operation flowchart of FIG. 2, the operations of steps S1 to S3 are performed by the operator (measuring person) of the TWA measuring electrocardiograph, and those of steps S4 to S8 are performed by the electrocardiograph controlling section 117. The operations of steps S1 to S9 correspond also to the procedure of the TWA measuring method of Embodiment 1. The operations of step S9 is performed by the TWA measuring section 118.

<Step S1>

In order to produce a 12-lead electrocardiogram, the operator of the TWA measuring electrocardiograph 110 shown in FIG. 1 attaches the measurement electrodes 115 to predetermined portions of the body surface of the patient. Since the TWA measuring electrocardiograph 110 of Embodiment 1 targets 12-lead electrocardiograms which are produced by various measuring methods, the measurement electrodes 115 are attached respectively to measurement portions of the patient which are determined in the employed measuring method. In the case where a synthesized 12-lead electrocardiogram of the type in which V1, V3, V4, and V6 are synthesized from 4 leads I, II, V2, and V5 is to be produced, for example, the measurement electrodes 115 are attached to a total of six places, i.e., four places or the right and left arms (electrodes L, R) and the right and left lower limbs (electrodes LL, RL) in order to acquire electrocardiographic signals of leads I and II, and two places or the lower left sternal edge of the fourth intercostal space, and the intersection of the left anterior axillary line with a horizontal line crossing the fifth intercostal space in order to acquire two chest leads (lead V2 and lead V5) electrocardiographic signals. In the case where a standard 12-lead electrocardiogram is to be produced, ten measurement electrodes 115 are attached to a total of ten places, i.e., six places for measuring chest leads, and four places for measuring four limb leads.

<Step S2>

Next, the operator inputs patient information through the patient information inputting section 111. For example, the specific ID "C123" and individual ID "A123" are input as the patient ID, and then the name of the patient, the age of the patient, and the sex of the patient are input.

<Step S3>

Then, the operator turns ON a measurement switch (not shown) of the TWA measuring electrocardiograph 110. When the measurement switch is turned ON, the measurement of the presence of TWA is started.

<Step S4>

The electrocardiograph controlling section 117 produces a 12-lead electrocardiogram from electrocardiographic signals of the six measurement electrodes 115 which are attached in step S1 to the patient.

In the case where the synthesized 12-lead electrocardiogram is to be produced, electrocardiographic signals (measurement lead vector) of four leads, i.e., leads I and II, and two chest leads (lead V2 and lead V5) are substituted in the following matrix formula, and the measurement lead vector is multiplied with a transformation matrix, thereby producing a synthesized electrocardiogram of the remaining four chest leads which are not actually detected by the measurement electrodes 115, i.e., lead V1, lead V3, lead V4, and lead V6 (synthesized lead vector).

$$\begin{bmatrix} V1 \\ V3 \\ V4 \\ V6 \end{bmatrix} = \begin{bmatrix} T1I & T1II & T12 & T15 \\ T3I & T3II & T32 & T35 \\ T4I & T3II & T42 & T45 \\ T6I & T6II & T62 & T65 \end{bmatrix} \begin{bmatrix} VI \\ VII \\ V2 \\ V5 \end{bmatrix}$$

where $$\begin{bmatrix} V1 \\ V3 \\ V4 \\ V6 \end{bmatrix}$$

is the synthesized lead vector, $$\begin{bmatrix} T1I & T1II & T12 & T15 \\ T3I & T3II & T32 & T35 \\ T4I & T3II & T42 & T45 \\ T6I & T6II & T62 & T65 \end{bmatrix}$$

is the transformation matrix, and $$\begin{bmatrix} VI \\ VII \\ V2 \\ V5 \end{bmatrix}$$

is the measurement lead vector.

Finally, a 12-lead electrocardiogram is produced.

In the case where the standard 12-lead electrocardiogram is to be produced, based on the electrocardiographic signals detected by the ten measurement electrodes, six limb lead waveforms (I, II, III, aVR, aVL, and aVF) of standard 12 leads, and six chest lead waveforms (V1, V2, V3, V4, V5, and V6) of standard 12 leads are calculated, and a 12-lead electrocardiogram is finally produced.

<Steps S5 to S7>

Next, the electrocardiograph controlling section 117 acquires the transformation coefficient for deriving a Frank's vector electrocardiogram, from the transformation coefficient storing section 114.

The electrocardiograph controlling section 117 determines whether a personal coefficient coincident with the patient information which is input in step S2 exists in the personal coefficient database 113A or not. Specifically, it is determined whether a personal coefficient coincident with the specific ID "C123" and individual ID "A123" which are input from the patient information inputting section 111 exists in the personal coefficient database 113A or not.

If a personal coefficient coincident with the patient information is in the personal coefficient database 113A, the electrocardiograph controlling section 117 acquires the personal coefficient of the patient from the personal coefficient database 113A. Personal coefficients are stored for respective patients and in time series. In the case where a plurality of personal coefficients exist for the patient, therefore, the latest personal coefficient is acquired.

By contrast, if a personal coefficient coincident with the patient information is not in the personal coefficient database 113A, the electrocardiograph controlling section 117 acquires a group coefficient coincident with the age and sex of the patient which are input as the patient information, from the group coefficient database 113B.

<Step S8>

The electrocardiograph controlling section 117 synthesizes a Frank's vector electrocardiogram from the 12-lead electrocardiogram which is produced in step S4, by using a transformation coefficient which is either one of the personal coefficient specific to the patient or group coefficient that is acquired in steps S5 to S7.

The process of deriving a Frank's vector electrocardiogram will be specifically described with reference to the operation flowchart of FIG. 3.

<Step S9>

The TWA measuring section 118 measures the presence of TWA from the Frank's vector electrocardiogram which is synthesized in step S8.

As described above, several techniques for measuring the presence of TWA have been known. One of the techniques is the technique which is disclosed in U.S. Pat. No. 4,802,491, which is based on spectral analysis, and which is said that the technique is most useful in the clinical site. In the technique based on spectral analysis, vector magnitude waveforms for 128 consecutive beats in which the HR is equal to or smaller than 110 during a period when a burden is applied to the subject are required.

When the waveforms are affected by noises or the conditions of HR=110 or less are not satisfied, therefore, the beat counting is not started. Considering that the time period between the ST and the T is changed depending on the HR, it is desirable to keep the HR constant as far as possible. In practice, however, the HR is hardly kept constant. Even in the case where the HR can be kept constant, an abnormal value may be included in the 128 beats.

In Embodiment 1, in order to eliminate such a trouble in the technique based on spectral analysis, first, waveforms of 128 or more beats, for example, 150 beats in which the HR is from 105 to 110 are selected from beats in a fixed zone. Basically, the selected 150 beats are consecutive. In the case where the beats are not consecutive, the selection is performed so as to maintain the alternation. For example, the selection in which the alternation is maintained is performed by setting the number of the unselected beats which are sandwiched between selected beats, to be even, or using, for example, the shape similarity of selected beats.

When vector magnitude waveforms for 150 beats are extracted by such a technique, the necessity of keeping the HR constant during the burdening is eliminated, and therefore the presence of TWA can be easily measured.

Next, waveforms for 128 beats in which correlations between the waveforms are equal to or larger than a predetermined threshold are selected from the selected vector magnitude waveforms for 150 beats.

In the case where an abnormal value (outlier) is included in the vector magnitude waveforms for 128 beats, moreover, the abnormal value is corrected by using another value.

As a result of such a process, the influence of an abnormal value (outlier) can be reduced as far as possible, and the accuracy of the measurement of the presence of TWA which is finally obtained is improved.

The process of measuring the presence of TWA will be specifically described with reference to the operation flowchart of FIG. 5.

Figure 3:
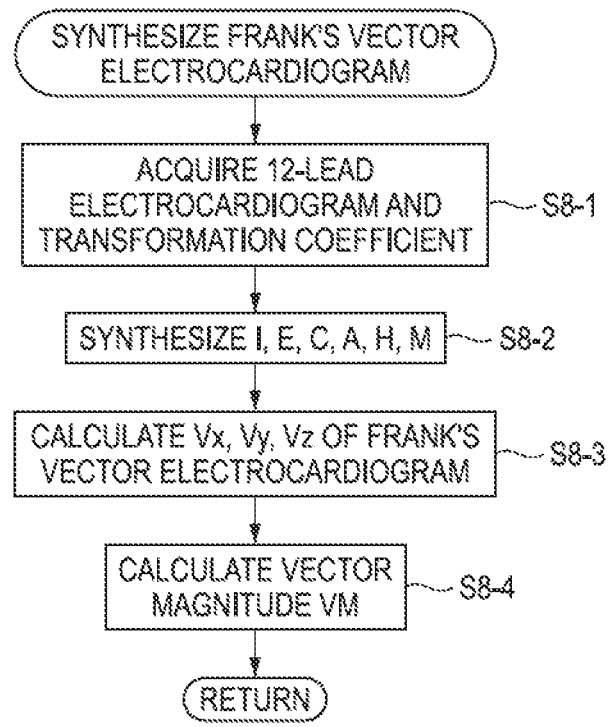
FIG. 3 is a flowchart showing procedures for deriving a Frank's vector electrocardiogram in the TWA measuring electrocardiograph of Embodiment 1.

The operation flowchart of FIG. 3 shows the procedure for deriving a Frank's vector electrocardiogram. The flowchart is a subroutine flowchart of step S8 in FIG. 2.

<Step S8-1>

The electrocardiograph controlling section 117 acquires the 12-lead electrocardiogram which is produced in step S4, and either one of the personal coefficient acquired in step S6 or the group coefficient acquired in step S7, as the transformation coefficient.

<Step S8-2>

The electrocardiograph controlling section 117 multiplies the 12-lead electrocardiogram by the transformation coefficient to synthesize six leads I, E, C, A, H, and M of the Frank's vector electrocardiogram.

Before the multiplication of the transformation coefficient, the electrocardiograph controlling section 117 performs preprocessing for removing baseline wander of the produced 12-lead electrocardiogram, in order that the DC component of the 12-lead electrocardiogram is eliminated to align the baseline. Simultaneously, preprocessing for removing high-frequency components of the 12-lead electrocardiogram is performed in order to eliminate high-frequency noises, thereby smoothing the waveform of the 12-lead electrocardiogram.

A Frank's vector electrocardiogram can be acquired by the multiplication of the 12-lead electrocardiogram by the transformation coefficient because of the following principle.

Between a 12-lead electrocardiogram L and a Frank's vector electrocardiogram F, there is a relationship such as shown in Formula 1 below. In the formula, α represents a transformation coefficient.

$$L\alpha = F \qquad \text{Formula 1}$$

In Formula 1, specifically, L indicates an arrangement (n×8) of the 12-lead electrocardiogram, α indicates a transformation coefficient in which the personal coefficient or the group coefficient is used, and F indicates an arrangement (n×6) of the Frank's vector electrocardiogram.

In the example, in the case where a 12-lead electrocardiogram is to be measured, eight electrodes are used in order to measure leads I and II, lead V1, lead V2, lead V3, lead V4, lead V5, and lead V6. Therefore, the 12-lead electrocardiogram constitutes the arrangement of (n×8).

As shown in Formula 1, in order to synthesize the six leads I, E, C, A, H, and M of the Frank's vector electrocardiogram from the 12-lead electrocardiogram, it is requested to multiply the 12-lead electrocardiogram by the transformation coefficient α.

In order to synthesize the Frank's vector electrocardiogram from the 12-lead electrocardiogram, it is necessary to previously obtain the transformation coefficient α. Because of this, the TWA measuring electrocardiograph 110 of Embodiment 1 is provided with the two kinds of transformation coefficients, i.e., the personal coefficient specific to the patient, and the group coefficient which is the average of a plurality of transformation coefficients acquired from an unspecified number of persons of a statistically effective population.

When the personal coefficient specific to the patient is to be acquired, for example, the measurement electrodes 115 are attached to specific portions of the patient which are determined for producing the 12-lead electrocardiogram L (leads I and II, lead V1, lead V2, lead V3, lead V4, lead V5, and lead V6), and the 12-lead electrocardiogram is produced from the electrocardiographic signals of the measurement electrodes 115. Next, the measurement electrodes 115 are attached to specific portions of the patient which are determined for producing the Frank's vector electrocardiogram F (lead I, lead E, lead C, lead A, lead H, and lead M), and the Frank's vector electrocardiogram is produced from the electrocardiographic signals of the measurement electrodes 115. In the example, the produced 12-lead electrocardiogram L (leads I and II, lead V1, lead V2, lead V3, lead V4, lead V5, and lead V6), and the produced Frank's vector electrocardiogram F (lead I, lead E, lead C, lead A, lead H, and lead M) are substituted in following Formula 2, and the personal coefficient specific to the patient is obtained as the transformation coefficient α. The process for acquiring the personal coefficient which is the transformation coefficient will be described specifically in detail with reference to the flowchart of FIG. 11.

$$\alpha = (L^T L)^{-1} L^T F \qquad \text{Formula 2}$$

where $L^T$ represents the transposed matrix of the 12-lead electrocardiogram L, and $(L^T L)^{-1}$ represents the inverse matrix of $(L^T L)$.

As shown in Formula 1, the electrocardiograph controlling section 117 multiplies the 12-lead electrocardiogram L by the thus obtained transformation coefficient to synthesize lead I, lead E, lead C, lead A, lead H, and lead M of the Frank's vector electrocardiogram F.

<Step S8-3>

When the Frank's vector electrocardiogram F (lead I, lead E, lead C, lead A, lead H, and lead M) is synthesized, the electrocardiograph controlling section 117 then substitutes the values of lead I, lead E, lead C, lead A, lead H, and lead M in following Formula 3, thereby obtaining lead $V_X$, lead $V_Y$, and lead $V_Z$ of the Frank's vector electrocardiogram.

$$V_X = 0.61A + 0.171C - 0.781I,$$

$$V_Y = 0.655F + 0.345M - 1.0H,$$

$$V_Z = 0.133A + 0.736M - 0.264I - 0.374E - 0.231C.$$

The above formulae are denoted by Formula 3.

<Step S8-4>

Finally, the electrocardiograph controlling section 117 squares the values of the obtained lead $V_X$, lead $V_Y$, and lead $V_Z$, adds together the squared values, and calculates the square root of the sum of the squared values, thereby calculating the value of a vector magnitude VM.

In the above, the process which is performed when the Frank's vector electrocardiogram is to be synthesized has been described.

The process of the operation flowchart of FIG. 3 will be described with reference to the waveform charts of FIG. 4.

Figure 4:
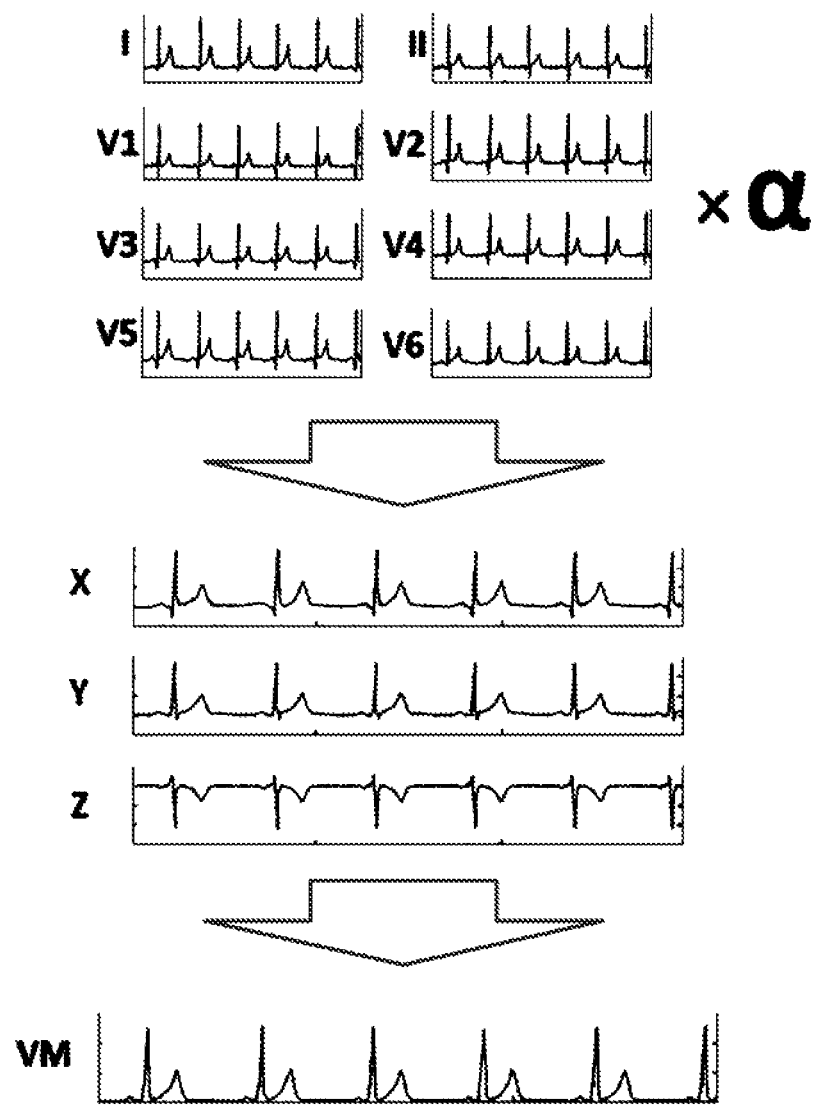
FIG. 4 shows waveform charts illustrating the process of the operation flowchart of FIG. 3.

When eight electrocardiogram waveforms of leads I and II, lead V1, lead V2, lead V3, lead V4, lead V5, and lead V6 are obtained as the 12-lead electrocardiogram L as shown in the upper waveform charts of FIG. 4, first, the processes of removing baseline wander and high-frequency components are applied on the electrocardiogram waveforms, and the transformation coefficient α is multiplied with the resulting waveforms.

Then, the values of lead I, lead E, lead C, lead A, lead H, and lead M are obtained, and electrocardiogram waveforms of lead $V_X$, lead $V_Y$, and lead $V_Z$ of the Frank's vector electrocardiogram are obtained as shown in the middle waveform charts of FIG. 4.

As shown in the lower waveform chart of FIG. 4, finally, an electrocardiogram waveform of the vector magnitude VM of the Frank's vector electrocardiogram is obtained from the values of lead $V_X$, lead $V_Y$, and lead $V_Z$. The presence of TWA which is to be finally obtained will be obtained from the electrocardiogram waveform of the vector magnitude VM.

Figure 5:
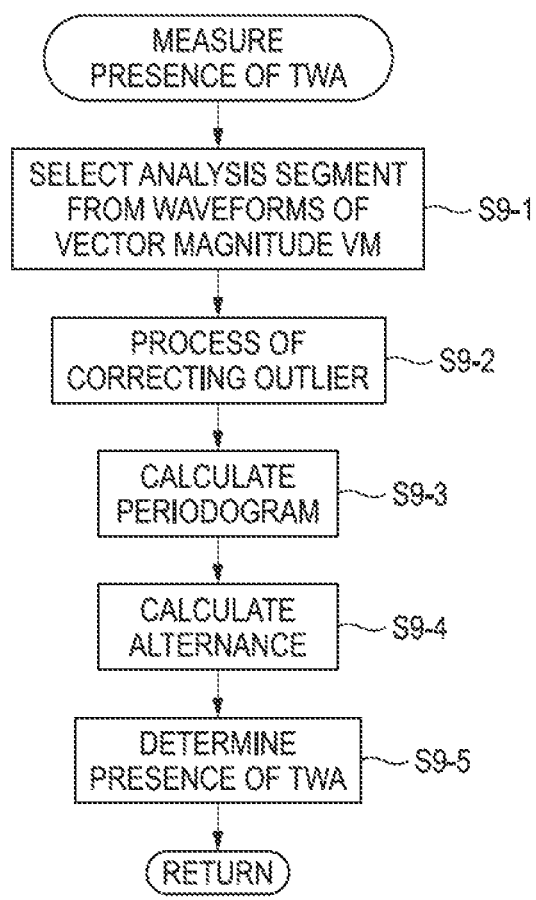
FIG. 5 is a flowchart showing procedures for measuring the presence of TWA in the TWA measuring electrocardiograph of Embodiment 1.

The operation flowchart of FIG. 5 shows the procedure for measuring the presence of TWA. The flowchart is a subroutine flowchart of step S9 in FIG. 2.

<Step S9-1>

The TWA measuring section 118 acquires the electrocardiogram waveform of the vector magnitude VM of the Frank's vector electrocardiogram which is obtained as described above, from the electrocardiograph controlling section 117. In order to improve the accuracy of the measurement of the presence of TWA, the TWA measuring section 118 eliminates an abnormal value and the like from the acquired electrocardiogram waveform of the vector magnitude VM, and selects waveforms which are used in the measurement of the presence of TWA.

First, the TWA measuring section 118 selects waveforms for 128 or more beats, for example, 150 beats.

Figure 7:
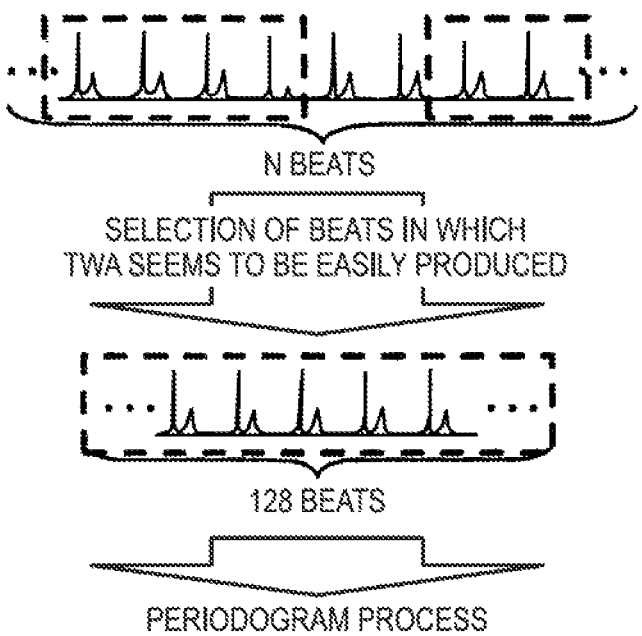
FIG. 7 is a view illustrating the process of selecting the analyzing segment.

In the selection of waveforms for 150 beats, as shown in FIG. 7, only beats in which the HR is from 105 to 110, and in which TWA seems to be easily produced are selected from the vector magnitude VM acquired from the electrocardiograph controlling section 117. It is preferable to select consecutive beats. In the case of consecutive 150 beats, however, there is a possibility that also noisy beats in which the presence of TWA is hardly measured may exist. This influences the measurement accuracy. Therefore, 150 beats in which TWA seems to be easily produced are inconsecutively selected.

There is a possibility that, in the thus selected vector magnitude waveforms for 150 beats, waveforms which are largely different in shape may be included. Next, therefore, the waveforms for 128 beats in which correlations between the waveforms are equal to or larger than a given threshold are selected from the vector magnitude waveforms for 150 beats.

Specifically, first, an average waveform which is obtained by averaging the vector magnitude waveforms for 150 beats in a first designated time period is acquired. Then, waveforms for 128 beats in which the correlations between the respective waveforms and the average waveform are equal to or larger than the given threshold are determined.

Then, ST-T segments of the thus selected vector magnitude waveforms for 128 beats are selected as an analysis segment.

<Step S9-2>

In the case where an outlier (abnormal value) is included in the analysis segment for 128 beats, the TWA measuring section 118 performs a process of correcting the outlier.

Outliers which seems to adversely affect the measurement of the presence of TWA are detected while being grouped into odd and even beats, and correction is performed on the detected beats.

Specifically, the intermediate value of the electrocardiogram waveforms is obtained for odd and even beats, and the standard deviation is obtained for odd and even beats. A threshold in which the standard deviation is used as a parameter, and which is used for determining an outlier is calculated, the magnitude relationship with respect to the threshold is determined, and an outlier is determined. The value which is determined as an outlier is substituted in a correction function in which the standard deviation is used as a parameter, and a correction value is calculated. Various methods of determining such a threshold, and correction functions are known. In the embodiment, any known method or function may be used.

Figure 8:
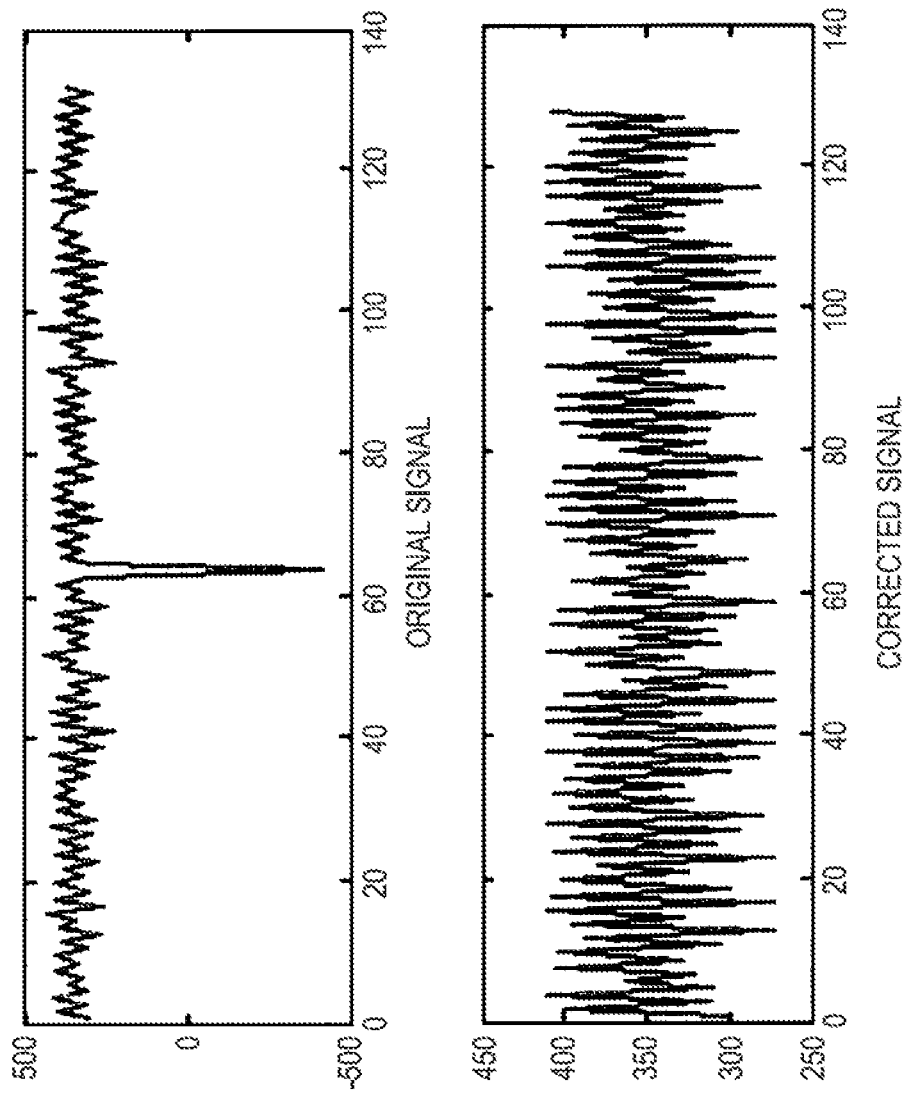
FIG. 8 shows waveform charts before and after performance of a process of correcting an outlier.

FIG. 8 shows waveform charts before and after performance of the process of correcting an outlier. In the waveform of the original signal which has not yet undergone the correcting process, as shown in the upper waveform chart of FIG. 8, a portion which largely drops in level exists in a middle portion. By contrast, in the waveform of the corrected signal which has undergone the correcting process, as shown in the lower waveform chart of FIG. 8, such a portion which largely drops in level does not exist in a middle portion. It is seen that the process of correcting an outlier achieves a significant effect.

<Step S9-3>

Figure 6:
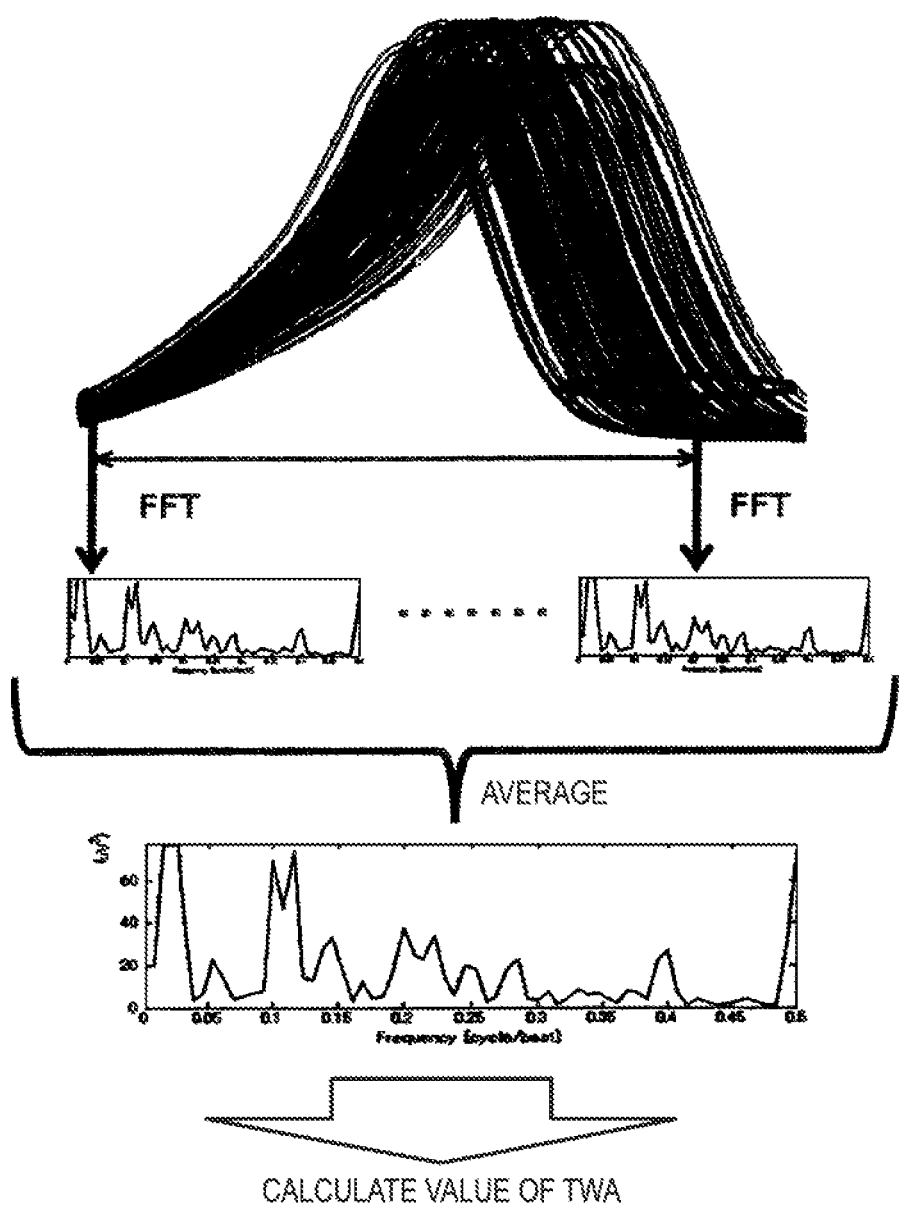
FIG. 6 is a view illustrating a process of selecting an analyzing segment.

After the outlier correction, as shown in FIG. 6, the TWA measuring section 118 performs the FFT process on the analysis segment for 128 beats, and calculates a periodogram.

Figure 9:
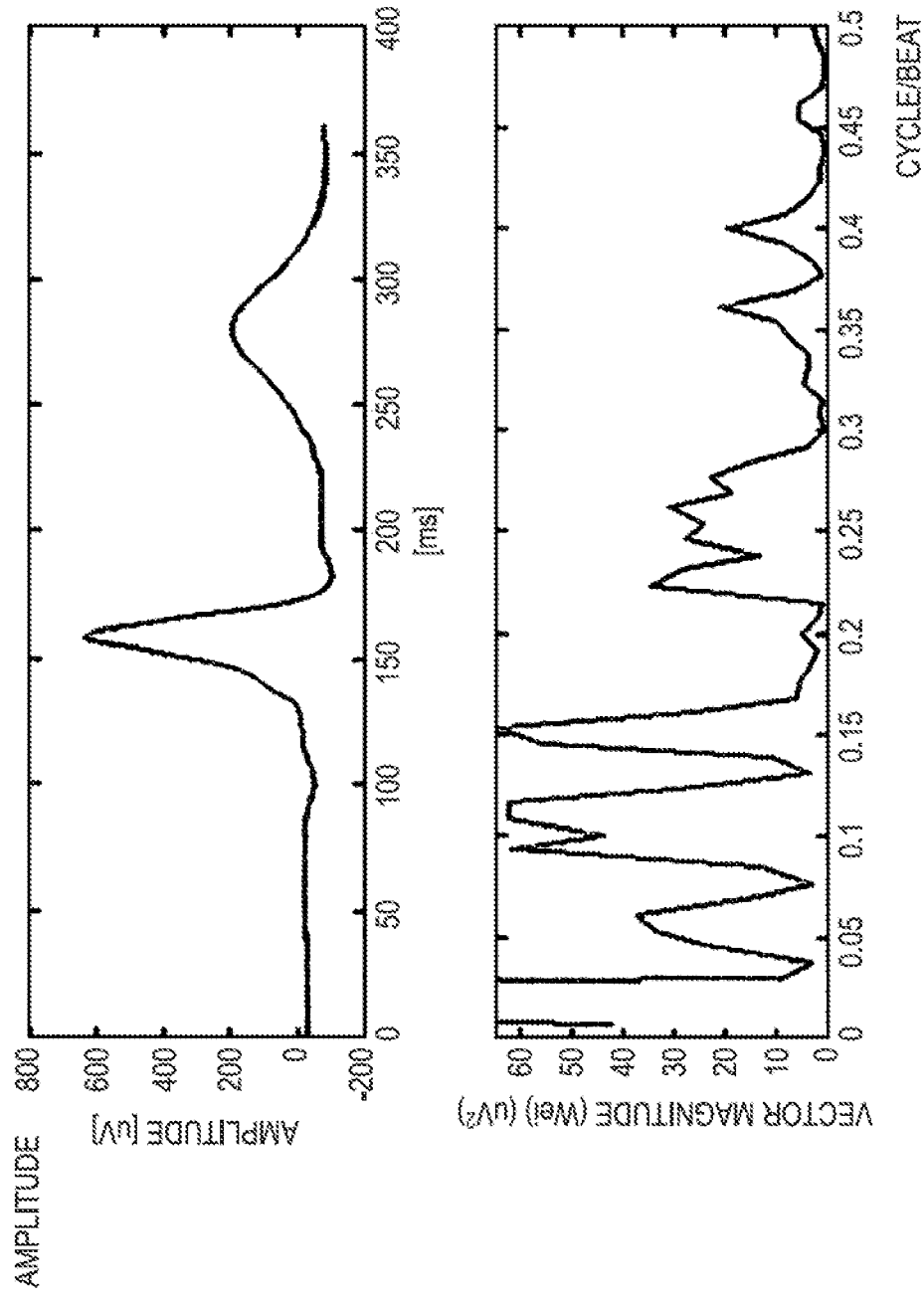
FIG. 9 is a view illustrating a process of calculating a periodogram.
Figure 10:
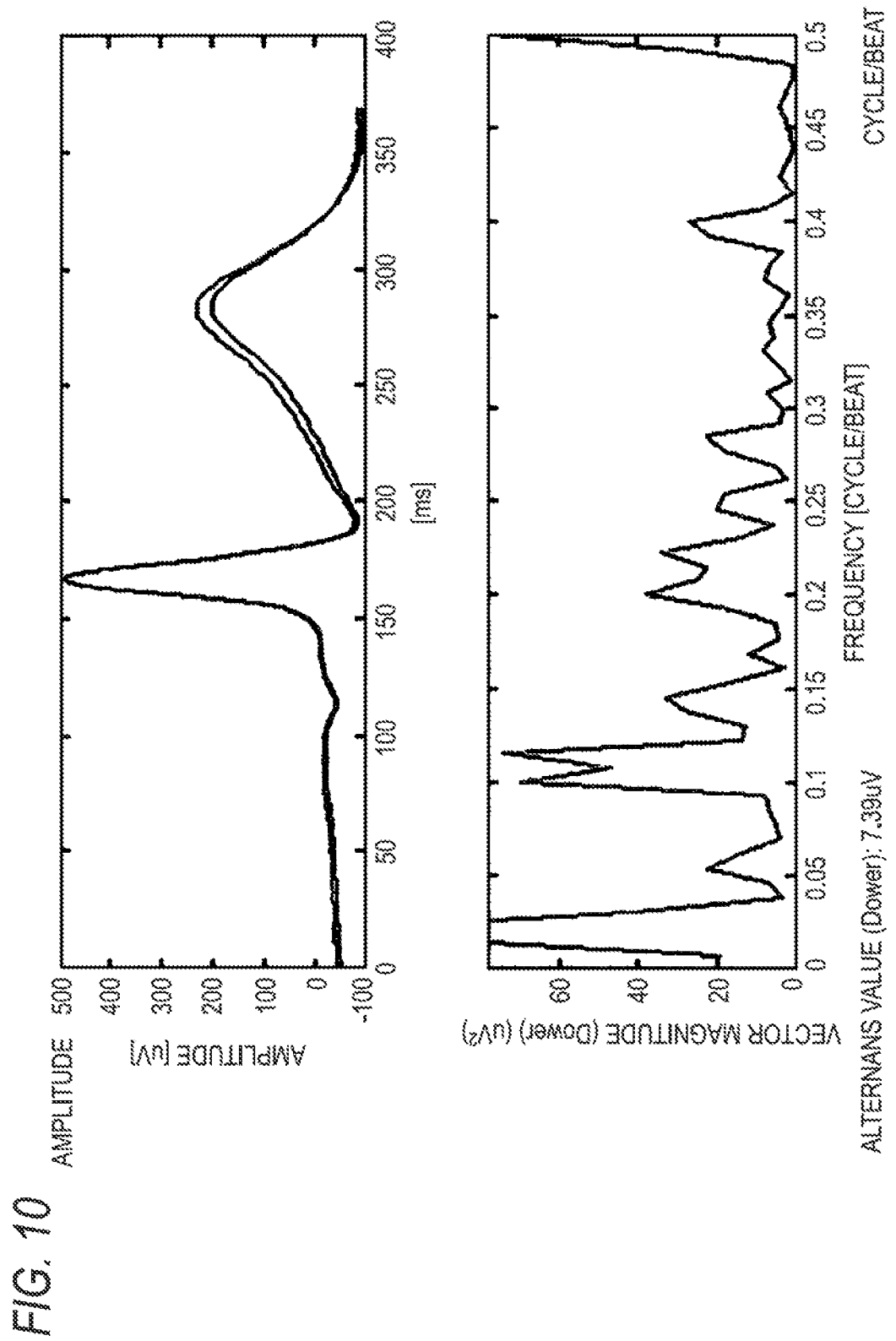
FIG. 10 is a view illustrating the process of calculating the periodogram.

FIGS. 9 and 10 are views for illustrating a periodogram. The upper waveform charts of FIGS. 9 and 10 show average waveforms of odd and even beats, respectively. The lower waveform charts of FIGS. 9 and 10 show waveforms which are obtained after a periodogram is calculated.

The waveform of FIG. 9 which is obtained after a periodogram is calculated shows that, when the frequency (cycle/beat) is 0.5, the value of the vector magnitude is small. This means that there is no TWA. By contrast, the waveform of FIG. 10 which is obtained after a periodogram is calculated shows that, when the frequency (cycle/beat) is 0.5, the value of the vector magnitude is large. This means that the value of TWA is large, and the possibility that TWA exists is large.

As described above, when a periodogram is calculated, the presence of TWA can be predicted to some extent from the magnitude of the value of the vector magnitude.

<Step S9-4>

Next, the TWA measuring section 118 calculates alternance. In the waveform charts which are shown in FIGS. 9 and 10, and which are obtained after a periodogram is calculated, the zone where the cycle/beat frequency is from 0.44 to 0.49 is defined as a noise band, and the average $S_{NB}$ and standard deviation $\sigma_{NB}$ of the zone are obtained. The value which is obtained when the cycle/beat frequency is 0.5 is indicated by $S_{0.5}$, and the following Formula 4 is calculated, thereby calculating alternance $V_{alt}$.

$$V_{alt}=(S_{0.5}-S_{NB})^{1/2} \quad \text{Formula 4}$$

<Step S9-5>

The TWA measuring section 118 determines the presence of TWA. By using the average $S_{NB}$ of the zone and value of alternance $V_{alt}$ which are calculated in step S9-4, the following Formula 5 is calculated, thereby calculating an alternance ratio k.

$$k=(V_{alt})^2/\sigma_{NB} \quad \text{Formula 5}$$

Then, the presence of TWA is determined from the values of the alternance $V_{alt}$ and the alternance ratio k. Conditions for determining the presence of TWA are the alternance $V_{alt}>1.9\ \mu V$ and the alternance ratio k>3. When the determination conditions are satisfied, it is determined that TWA exists.

As described above, when the waveform shape of a Frank's vector electrocardiogram obtained from a 12-lead electrocardiogram is analyzed, it is possible to determine the presence of TWA in which T waves having different shapes appear alternately at each beat (ABABAB . . . ).

In the case where the personal coefficient of the patient is not stored, next, the TWA measuring electrocardiograph 110 of Embodiment 1 causes the displaying section 116 to display the message for prompting the acquisition of the personal coefficient. At this time, the operator of the TWA measuring electrocardiograph 110 acquires the personal coefficient of the patient, and stores it in the personal coefficient database 113A of the TWA measuring electrocardiograph 110.

Figure 11:
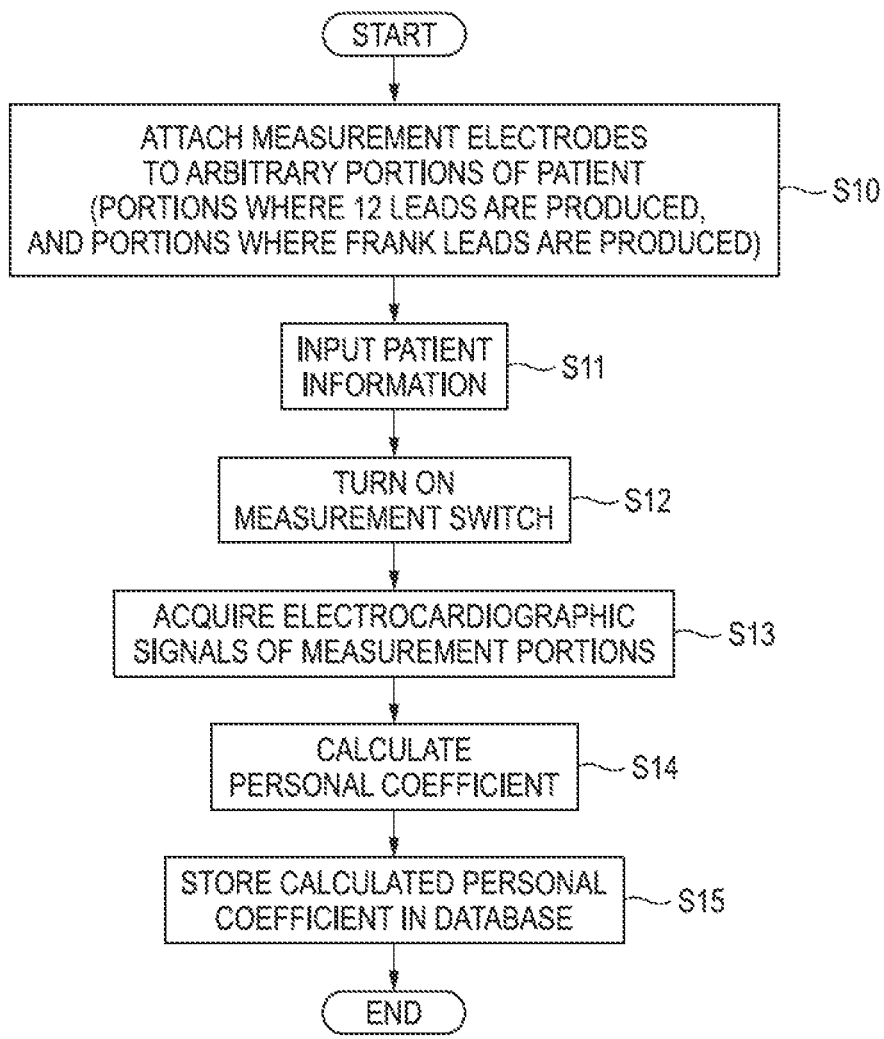
FIG. 11 is an operation flowchart of the TWA measuring electrocardiograph of Embodiment 1.

The procedure of this case will be described in detail with reference to the operation flowchart of FIG. 11. In the flowchart of FIG. 11, the operations of steps S10 to S12 are performed by the operator of the TWA measuring electrocardiograph 110, and those of steps S13 to S15 are performed by the electrocardiograph controlling section 117. The operations of steps S13 to S15 correspond to the procedure of the TWA measuring method of Embodiment 1.

<Step S10>

In order to acquire a 12-lead electrocardiogram and a Frank's vector electrocardiogram, first, the operator attaches the measurement electrodes to specific portions of the patient.

Specifically, the measurement electrodes 115 are attached to specific portions of the patient which are determined so as to produce a 12-lead electrocardiogram (leads I and II, lead V1, lead V2, lead V3, lead V4, lead V5, and lead V6), and attached to specific portions of the patient which are determined so as to produce a Frank's vector electrocardiogram (lead I, lead E, lead C, lead A, lead H, and lead M).

<Step S11>

Next, the operator inputs the patient information through the patient information inputting section 111. For example, the specific ID "C123" and the individual ID "A123" are input as the patient ID, and then the name and age of the patient are input.

<Step S12>

Then, the operator turns ON the measurement switch (not shown) of the TWA measuring electrocardiograph 110.

<Step S13>

The electrocardiograph controlling section 117 acquires electrocardiographic signals of the measurement portions from the measurement electrodes 115 attached to the patient.

<Step S14>

The electrocardiograph controlling section 117 produces a 12-lead electrocardiogram from the electrocardiographic signals of the measurement electrodes 115, and also a Frank's vector electrocardiogram from the electrocardiographic signals of the measurement electrodes 115. In the above example, the produced 12-lead electrocardiogram (leads I and II, lead V1, lead V2, lead V3, lead V4, lead V5, and lead V6), and the produced Frank's vector electrocardiogram (lead I, lead E, lead C, lead A, lead H, and lead M) are substituted in following Formula 6, and the personal coefficient specific to the patient is calculated as the transformation coefficient α.

$$\alpha = (L^T L)^{-1} L^T F \qquad \text{Formula 6}$$

where $L^T$ represents the transposed matrix of the 12-lead electrocardiogram L, and $(L^T L)^{-1}$ represents the inverse matrix of $(L^T L)$.

<Step S15>

The electrocardiograph controlling section 117 stores the calculated personal coefficient in the personal coefficient database 113A. When the personal coefficient is to be stored, the specific ID "C123" of the patient, the individual ID "A123" of the patient, and the name and age of the patient are added as additional information of the personal coefficient, and stored in time series.

In the above, the operations of the TWA measuring electrocardiograph and TWA measuring method of Embodiment 1 have been described.

(Configuration of TWA Measurement System)

Next, the configuration of the TWA measurement system in Embodiment 1 will be described. TWA measuring electrocardiographs 110, 120, 130, 210, 220, 230 of the TWA measurement system in Embodiment 1 are those which have been described in the embodiment above. Namely, the electrocardiographs can synthesized a Frank's vector electrocardiogram from a scalar electrocardiogram such as a 12-lead electrocardiogram, and can measure the presence of TWA from the Frank's vector electrocardiogram.

Figure 12:
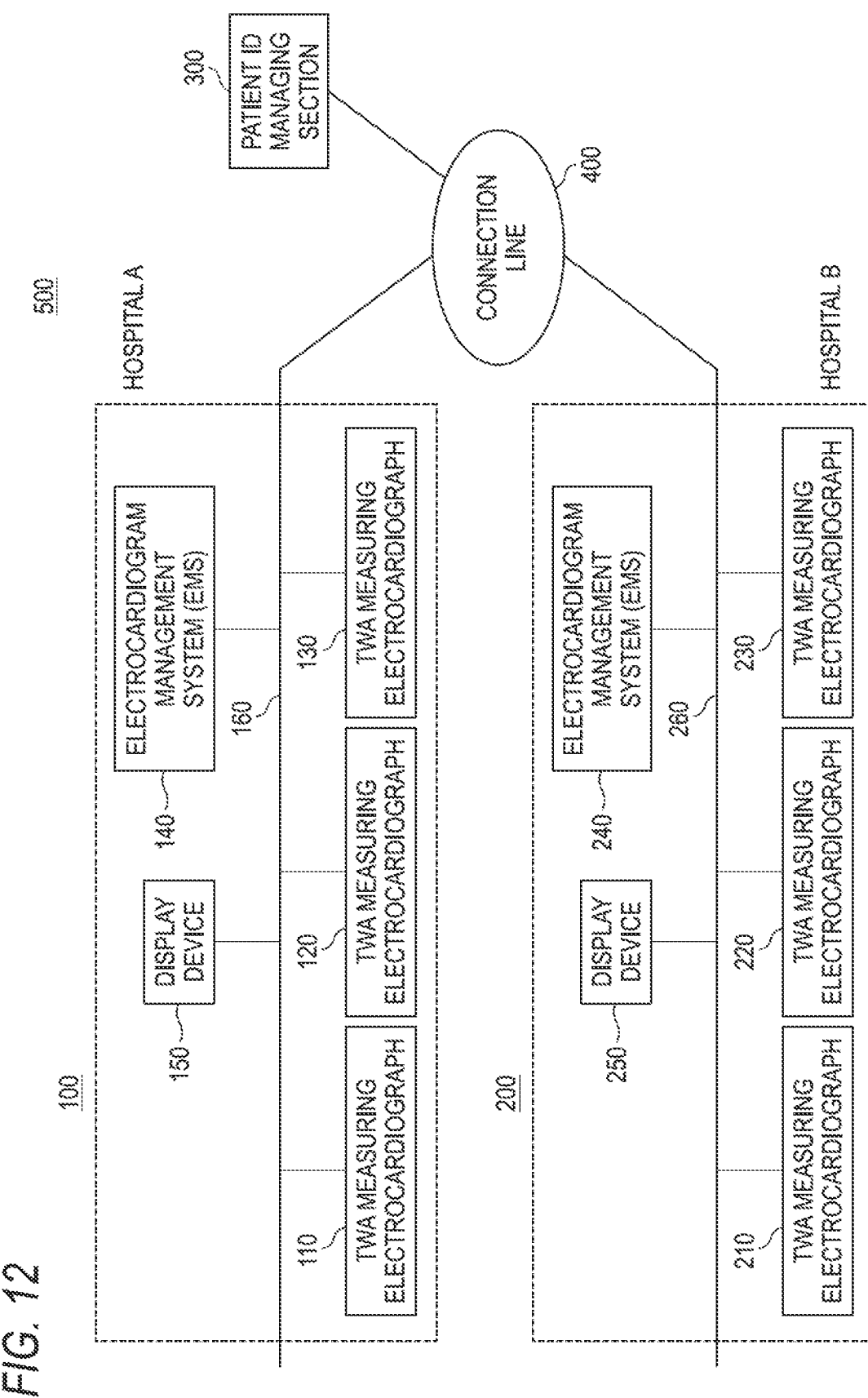
FIG. 12 is a block diagram of a TWA measurement system in Embodiment 1.

FIG. 12 is a block diagram of the TWA measurement system in Embodiment 1.

The TWA measurement system 500 has: an electrocardiogram management apparatus 100 provided in a hospital A; an electrocardiogram management apparatus 200 provided in a hospital B; a patient ID managing section 300 which manages patient IDs (specific IDs and individual IDs) in the hospitals A and B; and a connection line 400. The electrocardiogram management apparatuses 100, 200 and the patient ID managing section 300 are connected to one another through the connection line 400.

In Embodiment 1, the case where the electrocardiogram management apparatuses 100, 200 are provided in hospitals will be exemplified. The institutions in which the electrocardiogram management apparatuses 100, 200 are provided are not limited to hospitals. For example, they may be provided in institutions other than hospitals, such as a medical examination center, a clinic, a school, and a senior care facility which perform health checkup.

Although the patient ID managing section 300 is disposed outside the electrocardiogram management apparatuses 100, 200, the patient ID managing section 300 may be disposed in, for example, the electrocardiogram management apparatus 100 of the hospital A. The connection line 400 may be a dedicated line through which the electrocardiogram management apparatuses 100, 200 are connected to the patient ID managing section 300, or a wired or wireless Internet line in which security measures are taken.

The electrocardiogram management apparatus 100 of the hospital A includes the TWA measuring electrocardiographs 110, 120, 130, an electrocardiogram management system (EMS) 140, and a display device 150. The TWA measuring electrocardiographs 110, 120, 130, the electrocardiogram management system (EMS) 140, and the display device 150 are connected to one another through the intra-hospital network 160.

The electrocardiogram management apparatus 200 of the hospital B includes the TWA measuring electrocardiographs 210, 220, 230, an electrocardiogram management system (EMS) 240, and a display device 250. The TWA measuring electrocardiographs 210, 220, 230, the electrocardiogram management system (EMS) 240, and the display device 250 are connected to one another through an intra-hospital network 260.

The intra-hospital networks 160, 260 may be dedicated lines through which the TWA measuring electrocardiographs 110, 120, 130, 210, 220, 230, and the display devices 150, 250 are connected to one another a wired or wireless intranet line, or a wired or wireless Internet line in which security measures are taken.

As described above, the TWA measuring electrocardiographs 110, 120, 130, 210, 220, 230 have the functions of searching the personal coefficient of the patient, or the group coefficient, calculating and storing the personal coefficient of the patient, and measuring the presence of TWA. Therefore, programs for accomplishing the functions are installed in the TWA measuring electrocardiographs 110, 120, 130, 210, 220, 230.

The electrocardiogram management system 140 is connected to the TWA measuring electrocardiographs 110, 120, 130 through the intra-hospital network 160. The electrocardiogram management system 140 transmits and receives information relating to the TWA measurement, such as patient information, produced electrocardiogram data, and the personal coefficient to and from the TWA measuring electrocardiographs 110, 120, 130, and manages the information.

The electrocardiogram management system 240 is connected to the TWA measuring electrocardiographs 210, 220, 230 through the intra-hospital network 260. The electrocardiogram management system 240 transmits and receives information relating to the TWA measurement, such as patient information, produced electrocardiogram data, and the personal coefficient to and from the TWA measuring electrocardiographs 210, 220, 230, and manages the information.

The electrocardiogram management systems 140, 240 have functions of searching the personal coefficient of the patient which is requested by the TWA measuring electrocardiograph 110, 120, 130, 210, 220, or 230 through the connection line 400, and outputting the searched personal coefficient toward the TWA measuring electrocardiograph requesting it. Therefore, programs for accomplishing the functions are installed in the electrocardiogram management systems 140, 240.

The display device 150 receives information which is produced by the TWA measuring electrocardiographs 110, 120, 130, and which relates to the measurement of TWA of the patient, from the electrocardiogram management system 140, and displays information of the patient which is designated by the operator. Moreover, the display device displays information which is acquired by the TWA measuring electrocardiographs 110, 120, 130, and which relates to the TWA measurement.

The display device 250 receives information which is produced by the TWA measuring electrocardiographs 210, 220, 230, and which relates to the measurement of TWA of the patient, from the electrocardiogram management system 240, and displays information of the patient which is designated by the operator. Moreover, the display device displays information which is acquired by the TWA measuring electrocardiographs 210, 220, 230, and which relates to the TWA measurement.

The patient ID managing section 300 has a function of, when the electrocardiogram management systems 140, 240 mutually search the personal coefficient of a specific patient, transforming an individual ID which is provided to the same patient by another hospital, to an individual ID which is used in this hospital. For example, the case where, to the same patient, an individual ID "A123" is provided in the hospital A, and an individual ID "B456" is provided in the hospital B will be considered. In this case, the individual ID "A123" is transformed to "B456", and the individual ID "B456" is transformed to "A123".

In the transformation of the individual ID between the hospitals, the specific ID is used. In the world, the specific ID is the only one ID which is provided to the patient. The ID can be commonly used in all hospitals in the world, and is specific to the patient. Two or more IDs cannot be provided to the same patient. The patient ID managing section 300 has a comparison table of specific IDs and individual IDs. The comparison table is always updated in response to a request from the electrocardiogram management systems 140, 240.

Figure 13:
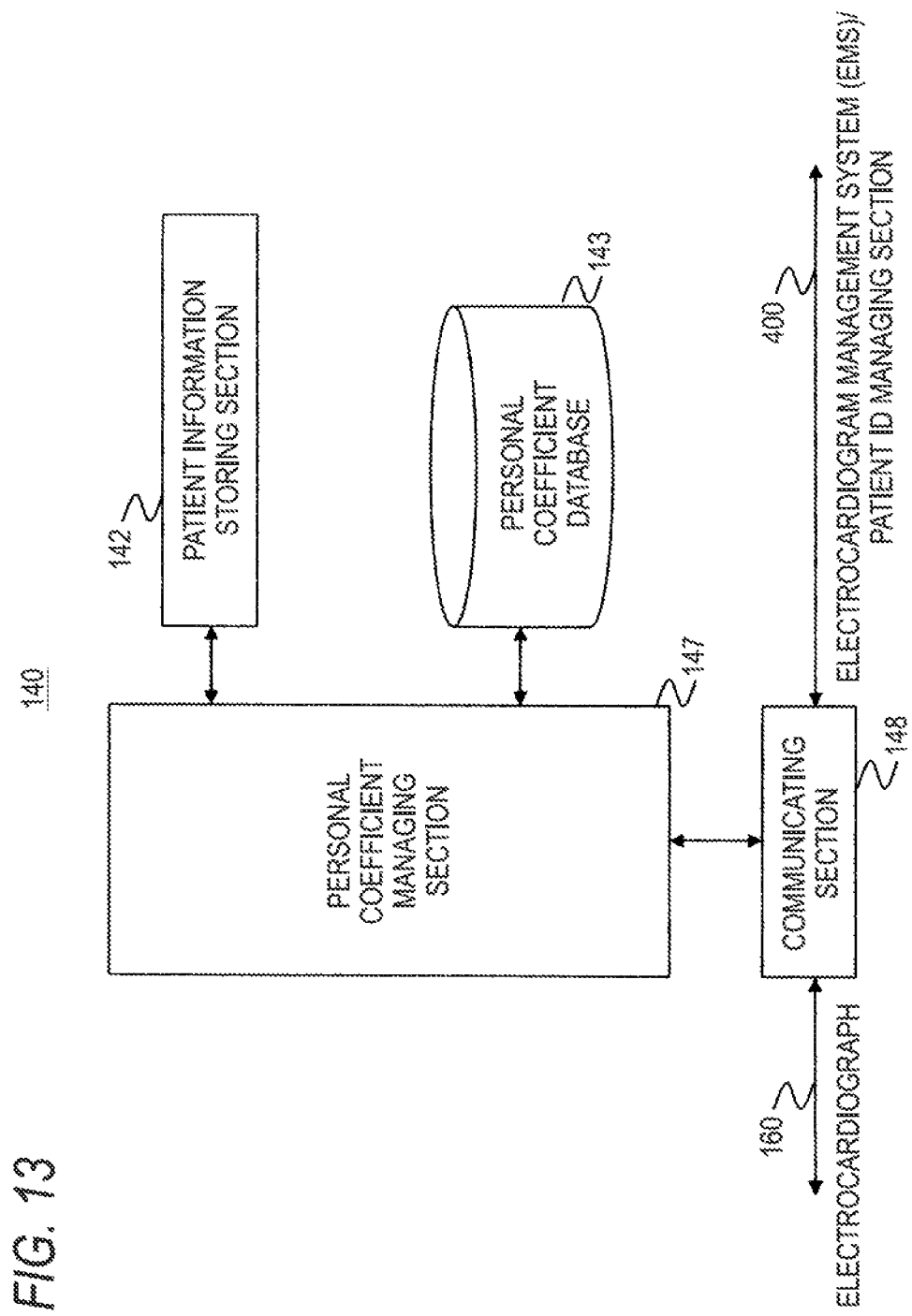
FIG. 13 is a block diagram of an electrocardiogram management system in Embodiment 1.

FIG. 13 is a block diagram of an electrocardiogram management system in Embodiment 1. Hereinafter, the configuration of the electrocardiogram management system 140 will be described. The electrocardiogram management system 240 is configured in the same manner as the electrocardiogram management system 140.

The electrocardiogram management system 140 includes a patient information storing section 142, a personal coefficient database 143, a personal coefficient managing section 147, and a communicating section 148.

The patient information storing section 142 stores patient information which is identical with that stored in the patient information storing sections of the TWA measuring electrocardiographs 110, 120, 130 (in the TWA measuring electrocardiograph 110, the patient information storing section 112). The patient information storing section 142 collectively stores all information stored in the TWA measuring electrocardiographs 110, 120, 130 connected to the intra-hospital network 160.

The personal coefficient database 143 stores personal coefficients which are identical with those stored in the personal coefficient databases of the TWA measuring electrocardiographs 110, 120, 130 (in the TWA measuring electrocardiograph 110, for example, the personal coefficient database 113A). The personal coefficient database 143 collectively stores all personal coefficients stored in the TWA measuring electrocardiographs 110, 120, 130 connected to the intra-hospital network 160.

The personal coefficient managing section 147 generally controls the operation of the electrocardiogram management system 140. The personal coefficient managing section 147 has functions of storing the patient information in the patient information storing section 142, and storing and fetching the personal coefficient of the patient in and from the personal coefficient database 143. The operation of the personal coefficient managing section 147 will be described later in detail.

The communicating section 148 receives the patient information and the personal coefficient from the TWA measuring electrocardiographs 110, 120, 130, and transmits the personal coefficient to the TWA measuring electrocardiographs 110, 120, 130. Furthermore, the communicating section 148 transmits the patient ID to the patient ID managing section 300, and receives the transformed patient ID. The transmission and reception of the patient information and the personal coefficient are performed through the intra-hospital network 160, and those of the patient ID are performed through the connection line 400.

Figure 14:
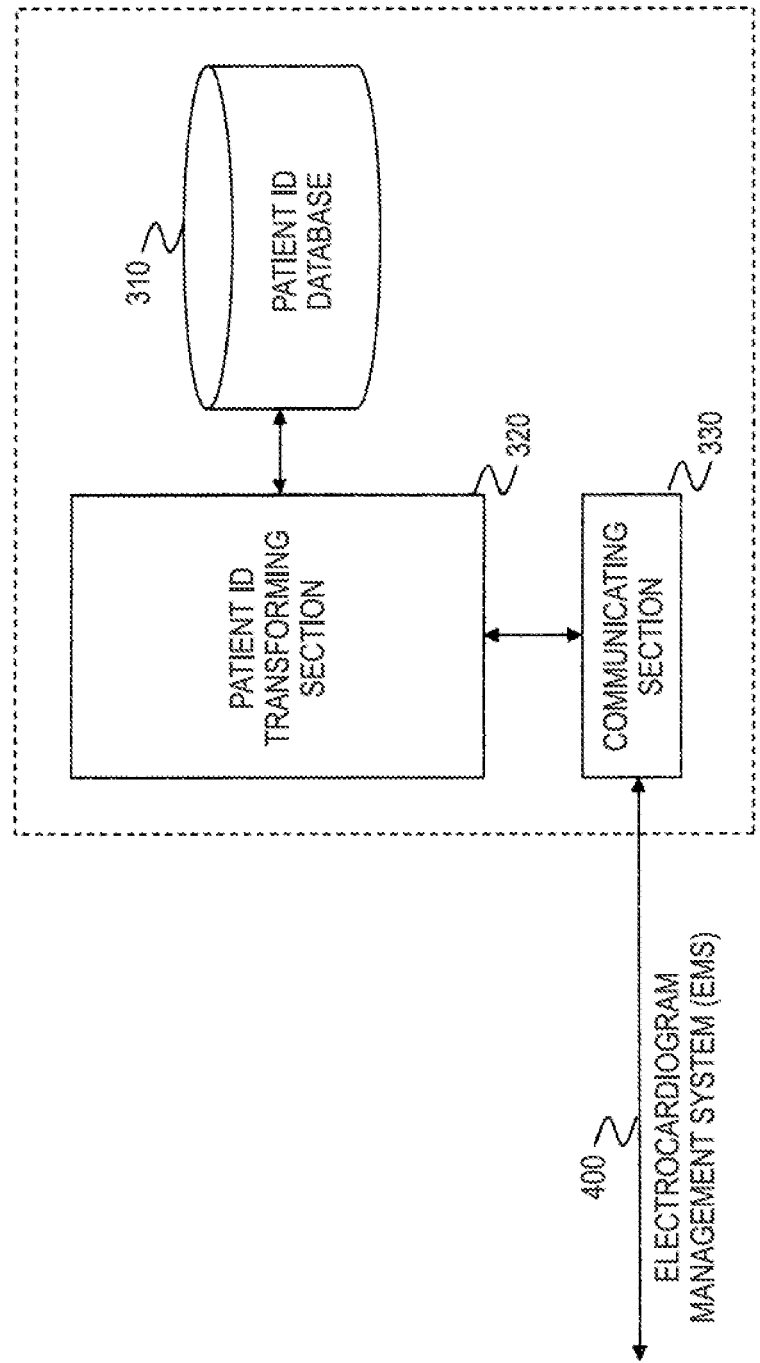
FIG. 14 is a block diagram of a patient ID managing section in Embodiment 1.

FIG. 14 is a block diagram of the patient ID managing section in Embodiment 1.

The patient ID managing section 300 includes a patient ID database 310, a patient ID transforming section 320, and a communicating section 330.

The patient ID database 310 stores correspondingly the specific and individual IDs of the patient. In the case where the specific ID is "C123", the individual ID in the hospital A is "A123", and that in the hospital B is "B456", for example, "C123"-"A123" and "C123"-"B456" are stored.

The patient ID transforming section 320 transforms the individual ID to that in the respective hospital while referring to the specific ID of the patient.

In the case where the hospital A is to search the personal coefficient in the hospital B, for example, the patient ID database 310 is accessed while referring to the specific ID of "C123", and the individual ID of "A123" in the hospital A is transformed to the individual ID of "B456" in the hospital B.

The communicating section 330 receives the specific and individual IDs of the patient transmitted from the electrocardiogram management systems 140, 240, and transmits the individual ID which is transformed in the patient ID transforming section 320, to the electrocardiogram management systems 140, 240.

The TWA measurement system in Embodiment 1 has the above-described configuration.

(Operation of TWA Measurement System)

Next, the operation of the TWA measurement system in Embodiment 1 will be described with reference to the operation flowcharts of FIGS. 15 to 23. The operation which is identical with that of the TWA measuring electrocardiograph will be briefly described.

Figure 15:
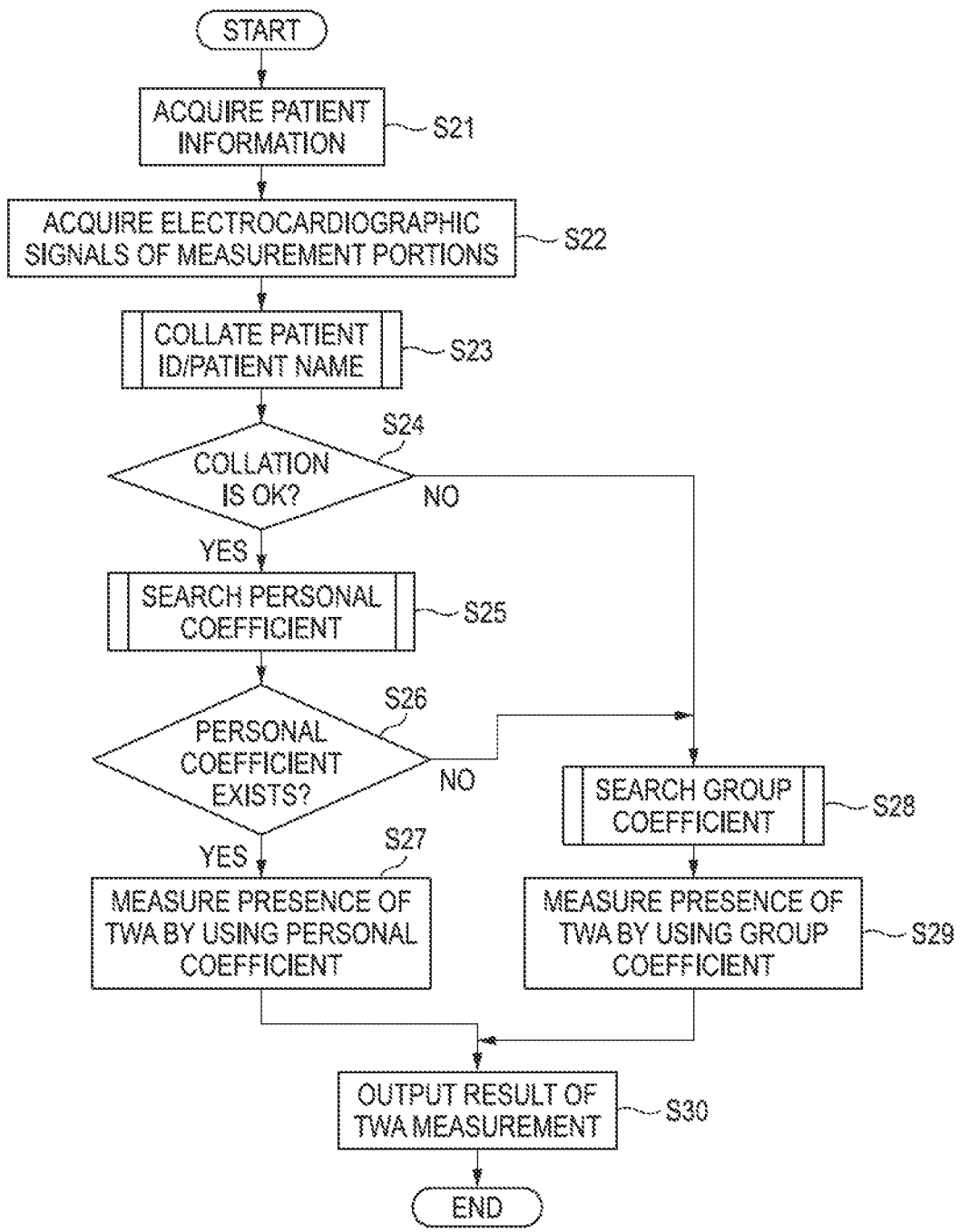
FIG. 15 is a main flowchart showing processes performed until when the TWA measuring electrocardiograph measures the presence of TWA in the TWA measurement system in Embodiment 1.

FIG. 15 is a main flowchart showing processes performed until when the TWA measuring electrocardiograph 110 outputs a result of the measurement of TWA of the patient. The main flowchart is performed by the electrocardiograph controlling section 117 of the TWA measuring electrocardiograph 110.

<Step S21>

The electrocardiograph controlling section 117 acquires the patient information supplied from the patient information inputting section 111. The patient information contains the patient ID (specific ID and individual ID), the name of the patient, the age of the patient, and the sex of the patient. The patient ID and the name of the patient are used for searching the personal coefficient of the patient, and the age and sex of the patient are used for searching the group coefficient.

<Step S22>

The electrocardiograph controlling section 117 acquires the electrocardiographic signals of the measurement portions from the measurement electrodes 115 which are attached to the patient.

<Step S23>

The electrocardiograph controlling section 117 collates the patient ID and the name of the patient with the patient ID and name of the patient which are stored in the patient information storing section 112.

<Steps S24, S25>

If there are a collating patient ID and a collating patient name in the patient information storing section 112, it is determined that the collation is OK (step S24: YES), and the personal coefficient stored in the personal coefficient database 113A or 143 or the personal coefficient database of the electrocardiogram management system 240 is searched.

<Steps S26, S27>

If there is the personal coefficient of the patient in either one of the personal coefficient database 113A or 143 or the personal coefficient database of the electrocardiogram management system 240 (step S26: YES), the electrocardiograph controlling section 117 acquires the personal coefficient of the patient from the one of the personal coefficient databases 113A, 143 and the personal coefficient database of the electrocardiogram management system 240. The electrocardiograph controlling section 117 processes the electrocardiographic signals acquired by the plural measurement electrodes 115, by using the acquired personal coefficient, and measures the presence of TWA.

<Step S28>

By contrast, if there is not a collating patient ID and a collating patient name in the patient information storing section 112 (step S24: NO), or if there is not the personal coefficient of the patient in any one of the personal coefficient databases 113A, 143 and the personal coefficient database of the electrocardiogram management system 240 (step S26: NO), the electrocardiograph controlling section 117 searches the group coefficient stored in the transformation coefficient storing section 114. While checking the age and sex of the patient, the electrocardiograph controlling section 117 acquires a group coefficient which is optimum to the patient, from the transformation coefficient storing section 114.

<Step S29>

The electrocardiograph controlling section 117 processes the electrocardiographic signals detected by the plural measurement electrodes 115, by using the acquired group coefficient, and measures the presence of TWA.

<Step S30>

The electrocardiograph controlling section 117 outputs a result of the measurement of the presence of TWA which is performed in Step S27 or Step S29, to the displaying section 116.

Figure 16:
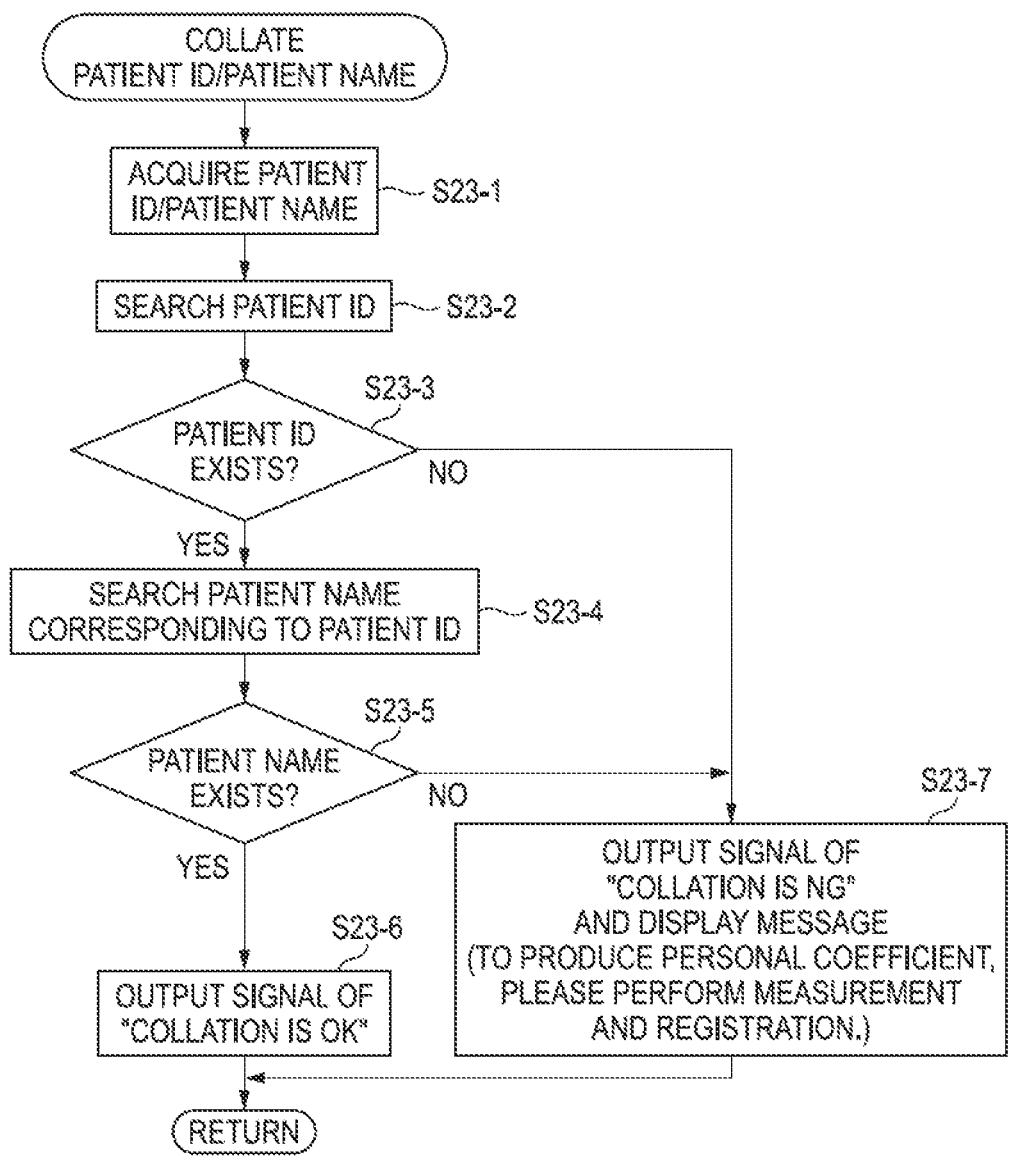
FIG. 16 is a subroutine flowchart of step S23 (COLLATE PATIENT ID/PATIENT NAME) in the main flowchart of FIG. 15.

FIG. 16 is a subroutine flowchart of step S23 (COLLATE PATIENT ID/PATIENT NAME) in the main flowchart of FIG. 15. The subroutine flowchart is performed by the electrocardiograph controlling section 117.

<Step S23-1>

The electrocardiograph controlling section 117 acquires the patient ID and the patient name in the patient information which is supplied from the patient information inputting section 111.

<Step S23-2>

The electrocardiograph controlling section 117 searches the patient ID stored in the patient information storing sections 112, 142.

<Steps S23-3, S23-4>

If there is the patient ID which is identical with that supplied from the patient information inputting section 111, in either one of the patient information storing section 112 or 142 (step S23-3: YES), the electrocardiograph controlling section 117 searches the patient name stored in the patient information storing section 112.

<Steps S23-5, S23-6>

If there is the patient name which is identical with that supplied from the patient information inputting section 111, in either one of the patient information storing section 112 or 142 (step S23-5: YES), a signal indicating that the collation is OK is output.

<Step S23-3, S23-5, S23-7>

If there is not a patient ID which is identical with that supplied from the patient information inputting section 111, in either one of the patient information storing section 112 or 142 (step S23-3: NO), or if there is not a patient name which is identical with that supplied from the patient information inputting section 111, in either one of the patient information storing section 112 or 142 (step S23-5: NO), a signal indicating that the collation is NG is output, and the electrocardiograph controlling section 117 causes the displaying section 116 to display a message "To produce personal coefficient, please perform measurement and registration."

Namely, if the input patient ID and patient name coincide with those which are registered in the TWA measuring electrocardiograph 110 or the electrocardiogram management system 140, it is determined that the collation is OK, and, if one of the patient ID and the patient name fails to be coincident, it is determined that the collation is NG. In the case where the collation is NG, the personal coefficient of the patient is not stored in the personal coefficient databases 113A, 143, and therefore a message for prompting acquisition of the personal coefficient is output.

Figure 17:
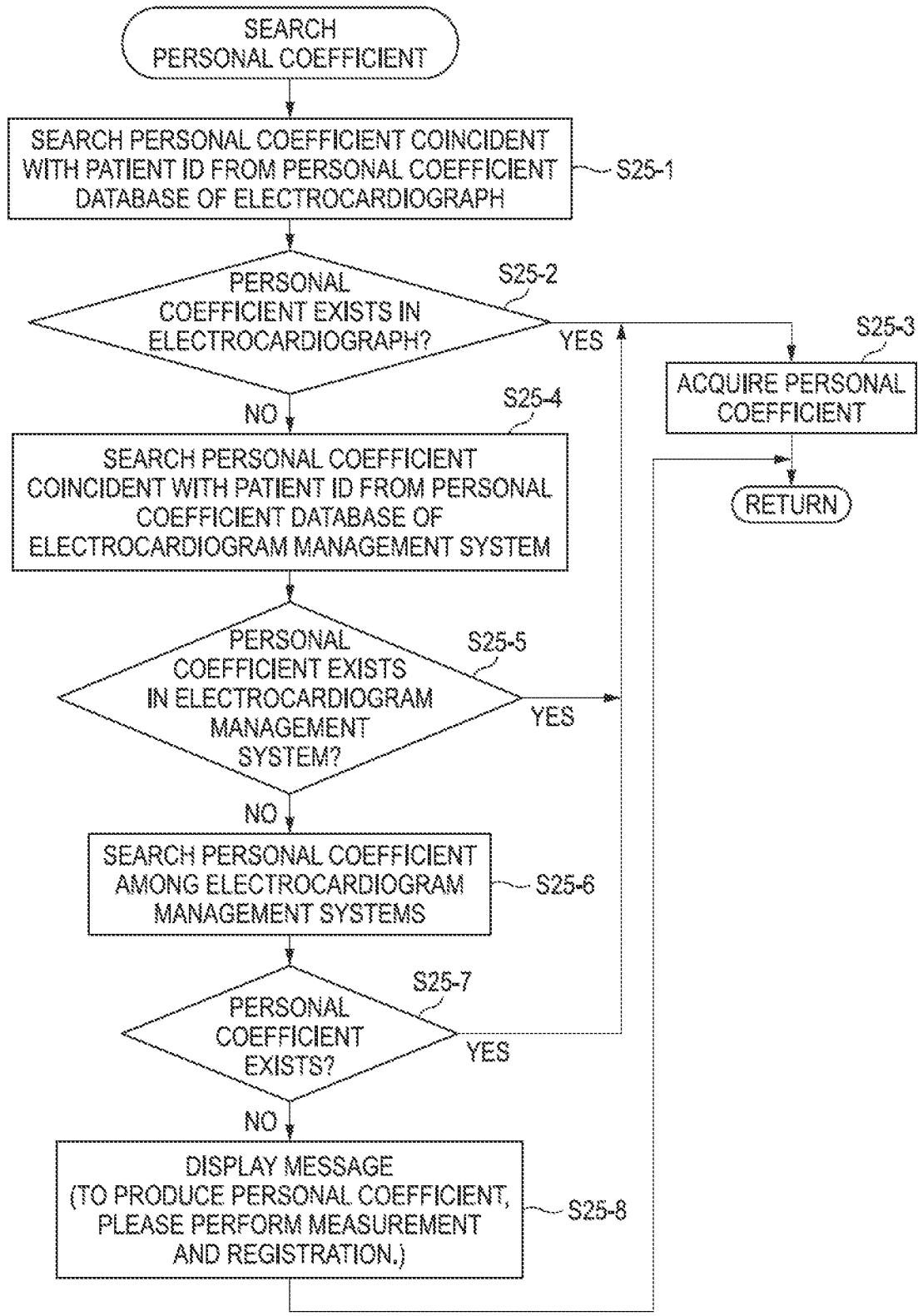
FIG. 17 is a subroutine flowchart of step S25 (SEARCH PERSONAL COEFFICIENT) in the main flowchart of FIG. 15.

FIG. 17 is a subroutine flowchart of step S25 (SEARCH PERSONAL COEFFICIENT) in the main flowchart of FIG. 15. The subroutine flowchart is performed by the electrocardiograph controlling section 117.

<Step S25-1>

The electrocardiograph controlling section 117 searches a personal coefficient which coincides with the patient ID, in the personal coefficient database 113A of the TWA measuring electrocardiograph 110.

<Steps S25-2, S25-3>

If there is the personal coefficient of the patient in the TWA measuring electrocardiograph 110 (step S25-2: YES), the electrocardiograph controlling section 117 acquires the personal coefficient from the personal coefficient database 113A.

<Steps S25-2, S25-4>

By contrast, if there is not the personal coefficient of the patient in the TWA measuring electrocardiograph 110 (step S25-2: NO), the electrocardiograph controlling section 117 searches the personal coefficient coincident with the patient ID in the personal coefficient database 143 of the electrocardiogram management system 140. Namely, it is searched whether the personal coefficient of the patient exists in the electrocardiogram management system 140 or not.

<Steps S25-5, S25-3>

If the personal coefficient of the patient exists in the electrocardiogram management system 140 (step S25-5: YES), the electrocardiograph controlling section 117 acquires the personal coefficient from the personal coefficient database 143.

<Steps S25-5, S25-6>

By contrast, if the personal coefficient of the patient does not exist in the personal coefficient database 143 of the electrocardiogram management system 140 (step S25-5: NO), the electrocardiograph controlling section 117 searches the personal coefficient which is coincident with the patient ID, among the electrocardiogram management systems 140, 240. In Embodiment 1, the personal coefficient which is coincident with the patient ID and the type of the result of the TWA measurement is searched from the electrocardiogram management system 240. The search of the personal coefficient among the electrocardiogram management systems 140, 240 is performed by using the personal ID which is transformed by the patient ID transforming section 320 while using the specific ID of the patient.

<Steps S25-7, S25-3>

If the personal coefficient of the patient exists in the electrocardiogram management system 240 (step S25-7: YES), the electrocardiograph controlling section 117 acquires the personal coefficient from the personal coefficient database of the electrocardiogram management system 240.

<Step S25-8>

If the personal coefficient of the patient does not exist in the personal coefficient database of the electrocardiogram management system 240, the electrocardiograph controlling section 117 causes the displaying section 116 to display a message "To produce personal coefficient, please perform measurement and registration."

Figure 18:
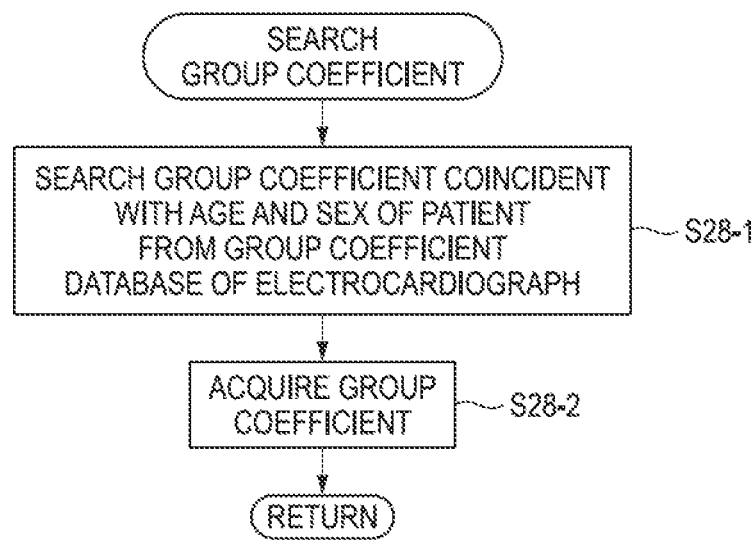
FIG. 18 is a subroutine flowchart of step S28 (SEARCH GROUP COEFFICIENT) in the main flowchart of FIG. 15.

FIG. 18 is a subroutine flowchart of step S28 (SEARCH GROUP COEFFICIENT) in the main flowchart of FIG. 15. The subroutine flowchart is performed by the electrocardiograph controlling section 117.

<Step S28-1>

The electrocardiograph controlling section 117 searches a group coefficient which coincides with the age and sex of the patient, in the group coefficient database 113B of the TWA measuring electrocardiograph 110. Namely, it is searched whether the group coefficient of the patient exists in the TWA measuring electrocardiograph 110 or not.

<Step S28-2>

The electrocardiograph controlling section 117 acquires the group coefficient from the group coefficient database 113B of the TWA measuring electrocardiograph 110.

Figure 19:
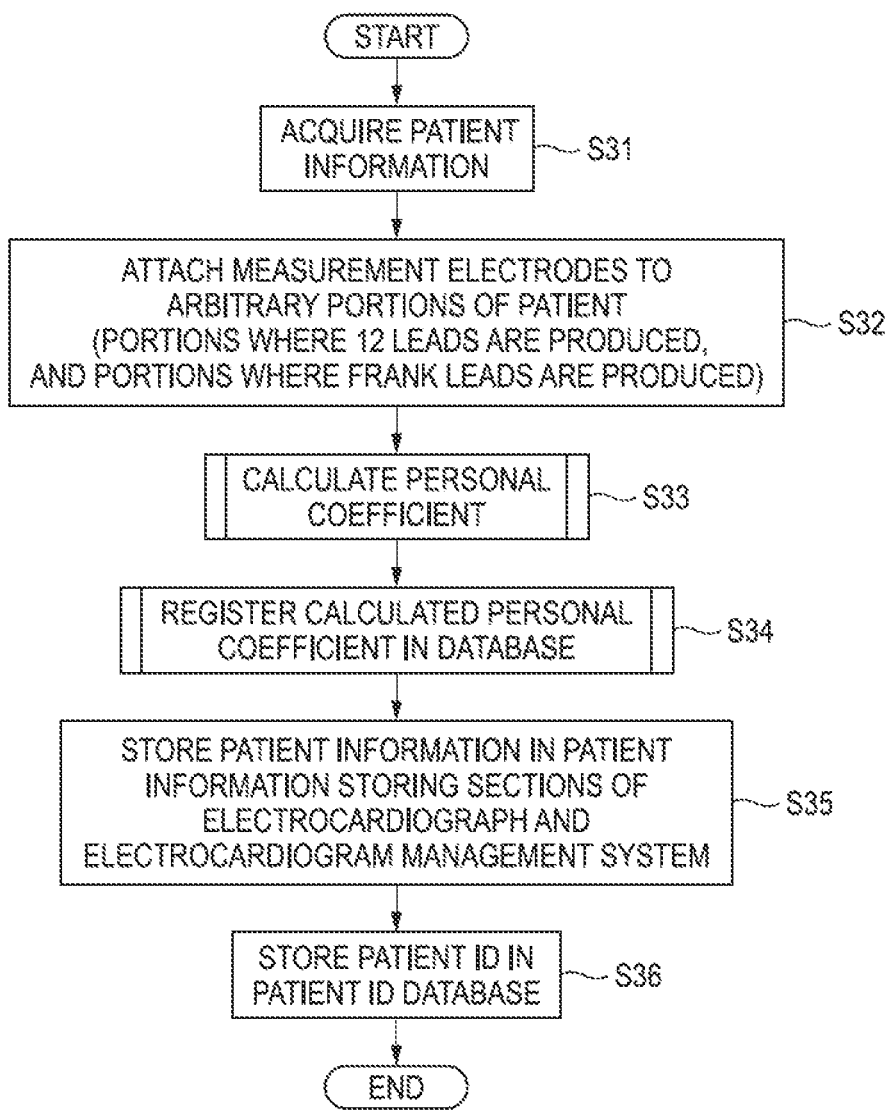
FIG. 19 is a main flowchart showing processes performed until when the personal coefficient of the patient is calculated and the calculated personal coefficient is stored in a personal coefficient database.

FIG. 19 is a main flowchart showing processes performed until when the personal coefficient of the patient is calculated and the calculated personal coefficient is stored in the personal coefficient database. The main flowchart is performed by the electrocardiograph controlling section 117.

<Step S31>

The electrocardiograph controlling section 117 acquires the patient information supplied from the patient information inputting section 111. The patient information contains the patient ID (specific ID and individual ID), the name of the patient, the age of the patient, and the sex of the patient. Among the patient information, the patient ID and the name of the patient are used for storing the patient coefficient of the patient in the personal coefficient database.

<Step S32>

The electrocardiograph controlling section 117 acquires electrocardiographic signals of arbitrary measurement portions from the measurement electrodes 115 which are attached to the patient. Specifically, for example, the measurement electrodes 115 are attached to specific portions of the patient which are determined so as to produce a 12-lead electrocardiogram (leads I and II, lead V1, lead V2, lead V3, lead V4, lead V5, and lead V6), and attached to specific portions of the patient which are determined so as to produce a Frank's vector electrocardiogram (lead I, lead E, lead C, lead A, lead H, and lead M). From the measurement electrodes 115, the electrocardiograph controlling section 117 measures leads I and II, lead V1, lead V2, lead V3, lead V4, lead V5, and lead V6 for a 12-lead electrocardiogram, and lead I, lead E, lead C, lead A, lead H, and lead M for a Frank's vector electrocardiogram.

<Step S33>

The electrocardiograph controlling section 117 substitutes the leads measured by means of the measurement electrodes 115, in above-described Formula 2 to calculate the personal coefficient α of the patient.

<Step S34>

Next, the electrocardiograph controlling section 117 stores the calculated personal coefficient in the database of the TWA measurement system, for each patient and in time series.

<Step S35>

The electrocardiograph controlling section 117 stores the patient information which is acquired in step S31, in the patient information storing section 112 of the TWA measuring electrocardiograph 110, and simultaneously stores the information in the patient information storing section 142 of the electrocardiogram management system 140. When the patient information is to be stored in the patient information storing section 142, the electrocardiograph controlling section 117 transmits the patient information from the communicating section 148 through the intra-hospital network 160, and the personal coefficient managing section 147 receives the patient information through the communicating section 148 of the electrocardiogram management system 140. Next, the patient information received by the personal coefficient managing section 147 is stored in the patient information storing section 142.

<Step S36>

Then, the electrocardiograph controlling section 117 stores the patient ID (specific ID and individual ID) of the patient information which is acquired in step S31, in the patient ID database 310 of the patient ID managing section 300. When the patient ID is to be stored in the patient ID database 310, the electrocardiograph controlling section 117 transmits the patient ID from the communicating section 148 through the intra-hospital network 160 and the connection line 400, and the patient ID transforming section 320 receives the patient ID through the communicating section 330 of the patient ID managing section 300. Next, the patient ID received by the patient ID transforming section 320 is stored in the patient ID database 310.

Figure 20:
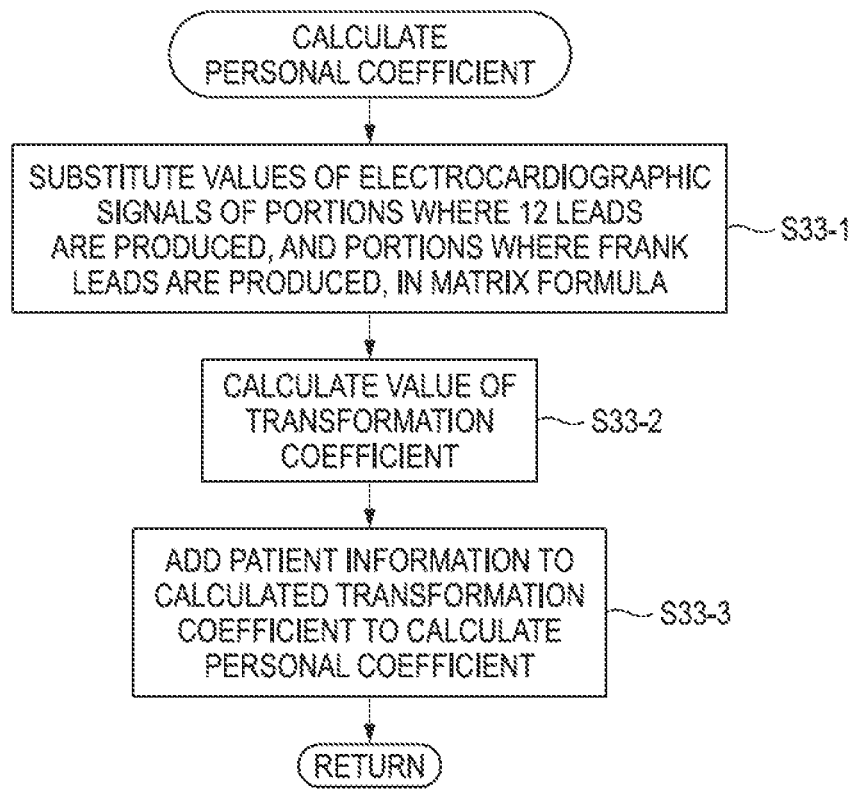
FIG. 20 is a subroutine flowchart showing a process of step S33 (CALCULATE PERSONAL COEFFICIENT) in the main flowchart of FIG. 19.

FIG. 20 is a subroutine flowchart showing a process of step S33 (CALCULATE OF PERSONAL COEFFICIENT) in the main flowchart of FIG. 19. The flowchart is performed by the electrocardiograph controlling section 117.

<Step S33-1>

The electrocardiograph controlling section 117 substitutes the 12-lead electrocardiogram (leads I and II, lead V1, lead V2, lead V3, lead V4, lead V5, and lead V6) and Frank's vector electrocardiogram (lead I, lead E, lead C, lead A, lead H, and lead M) which are measured by the measurement electrodes 115 attached to the patient, in above-described Formula 2.

<Step S33-2>

Next, the electrocardiograph controlling section 117 obtains the values of the transformation efficient from the values of leads I and II, lead V1, lead V2, lead V3, lead V4, lead V5, and lead V6, and those of lead I, lead E, lead C, lead A, lead H, and lead M.

<Step S33-3>

Finally, the electrocardiograph controlling section 117 adds the patient information to the obtained transformation coefficient to calculate the personal coefficient. Specifically, the patient information to be added contains the patient ID (specific ID and individual ID) and the patient name. In the above-described case, the specific ID "C123" of the patient, the individual ID "A123" of the patient, and the patient name are added as additional information, and the personal coefficient is calculated.

Figure 21:
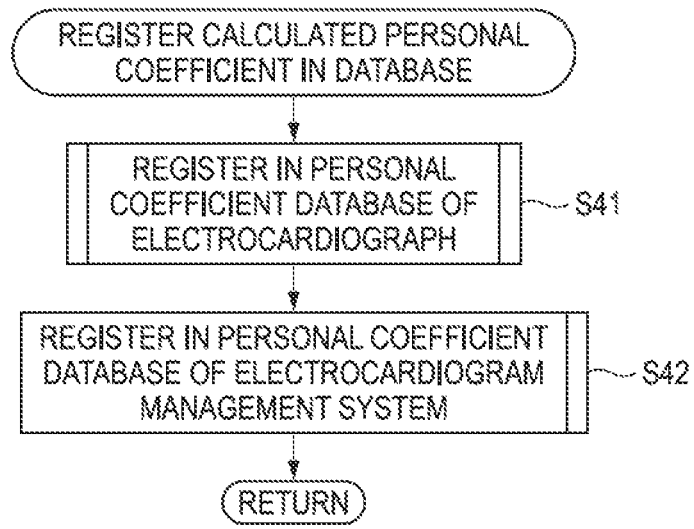
FIG. 21 is a subroutine flowchart showing a process of step S34 (REGISTER CALCULATED PERSONAL COEFFICIENT IN DATABASE) in the main flowchart of FIG. 19.

FIG. 21 is a subroutine flowchart showing a process of step S34 (REGISTER CALCULATED PERSONAL COEFFICIENT IN DATABASE) in the main flowchart of FIG. 19. The subroutine flowchart is performed by the electrocardiograph controlling section 117 and the personal coefficient managing section 147.

<Step S41>

First, the electrocardiograph controlling section 117 stores the calculated personal coefficient in the personal coefficient database 113A.

<Step S42>

Next, the personal coefficient managing section 147 stores the personal coefficient which is sent from the electrocardiograph controlling section 117, in the personal coefficient database 143. The processes of these steps are shown in detail in the subroutine flowcharts of FIGS. 22 and 23.

Figure 22:
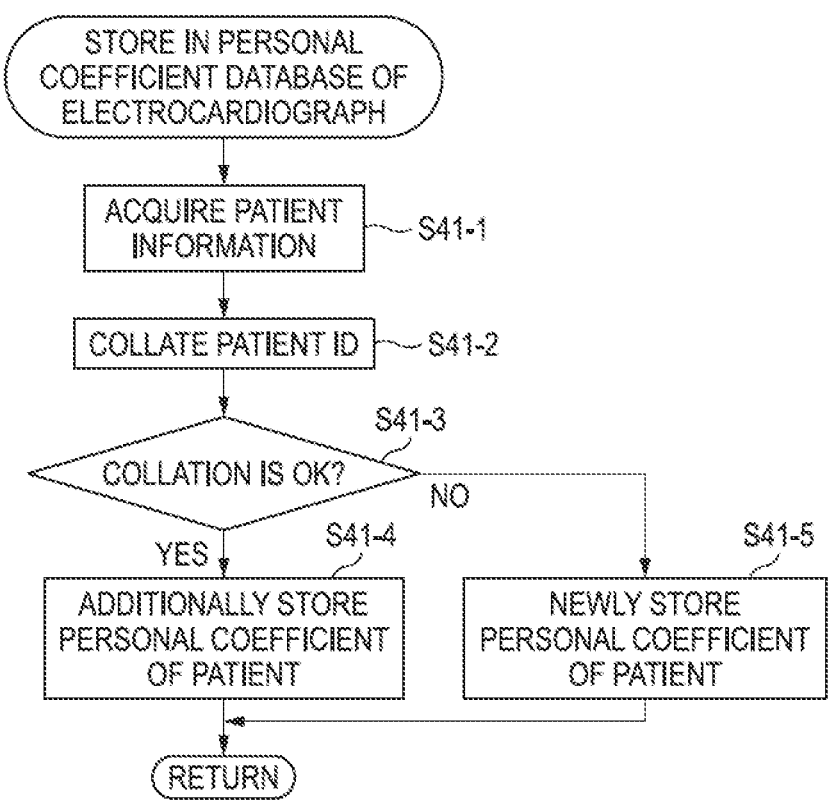
FIG. 22 is a subroutine flowchart showing a process of step S41 (STORE PERSONAL COEFFICIENT DATABASE OF TWA MEASURING ELECTROCARDIOGRAPH) in the subroutine flowchart of FIG. 21.

FIG. 22 is a subroutine flowchart showing a process of step S41 (STORE IN PERSONAL COEFFICIENT DATABASE OF TWA MEASURING ELECTROCARDIOGRAPH) in the subroutine flowchart of FIG. 21. The flowchart is performed by the electrocardiograph controlling section 117.

<Step S41-1>

First, the electrocardiograph controlling section 117 acquires the patient information supplied from patient information inputting section 111. The patient information contains the patient ID (specific ID and individual ID), the name of the patient, the age of the patient, and the sex of the patient.

<Step S41-2>

The electrocardiograph controlling section 117 collates the patient ID with that stored in the patient information storing section 112.

<Steps S41-3, S41-4>

If there is a collating patient ID in the patient information storing section 112, it is determined that the collation is OK (step S41-3: YES), and the electrocardiograph controlling section 117 additionally stores the personal coefficient of the patient in the personal coefficient database 113A. In the case where the same patient has already the personal coefficient, namely, the newly calculated personal coefficient is additionally stored in time series. When the personal coefficient is updated in time series, it is possible to always select the optimum coefficient of the patient, so that an accurate result of the TWA measurement can be produced.

<Steps S41-3, S41-5>

By contrast, if there is not a collating patient ID in the patient information storing section 112 and it is determined that the collation is NG (step S41-3: NO), the personal coefficient of the patient does not exist in the personal coefficient database 113A, and hence the electrocardiograph controlling section 117 newly stores the personal coefficient in the personal coefficient database 113A.

Figure 23:
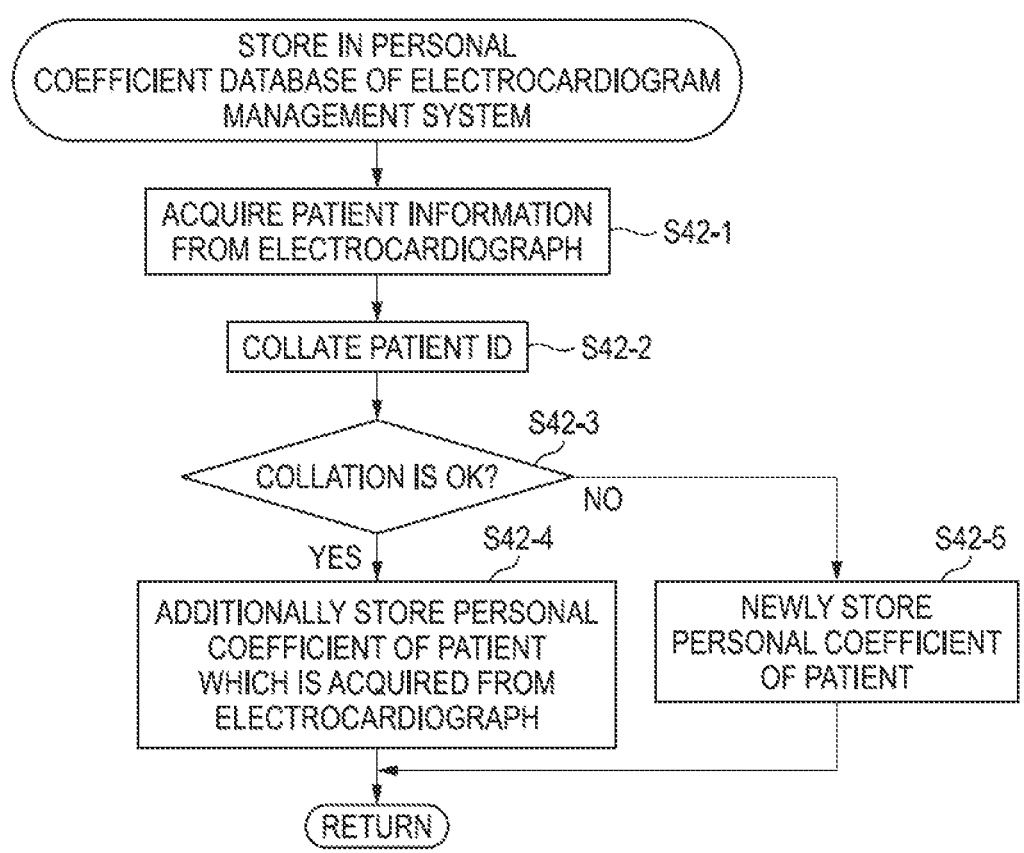
FIG. 23 is a subroutine flowchart showing a process of step S42 (STORE PERSONAL COEFFICIENT DATABASE OF ELECTROCARDIOGRAM MANAGEMENT SYSTEM) in the subroutine flowchart of FIG. 21.

FIG. 23 is a subroutine flowchart showing a process of step S42 (STORE IN PERSONAL COEFFICIENT DATABASE OF ELECTROCARDIOGRAM MANAGEMENT SYSTEM) in the subroutine flowchart of FIG. 21. The flowchart is performed by the personal coefficient managing section 147.

<Step S42-1>

First, the personal coefficient managing section 147 of the electrocardiogram management system 140 acquires the patient information from the TWA measuring electrocardiograph 110. The patient information contains the patient ID (specific ID and individual ID), the name of the patient, the age of the patient, and the sex of the patient.

<Step S42-2>

The personal coefficient managing section 147 collates the patient ID with that stored in the patient information storing section 142.

<Steps S42-3, S42-4>

If there is a collating patient ID in the patient information storing section 142, it is determined that the collation is OK (step S42-3: YES), the personal coefficient managing section 147 additionally stores the personal coefficient of the patient in the personal coefficient database 143. In the case where the same patient has already the personal coefficient, namely, the newly calculated personal coefficient is additionally stored in time series.

<Steps S42-3, S42-5>

By contrast, if there is not a collating patient ID in the patient information storing section 142 and it is determined that the collation is NG (step S42-3: NO), the personal coefficient of the patient does not exist in the personal coefficient database 143, and hence the personal coefficient managing section 147 newly stores the personal coefficient in the personal coefficient database 143.

As described above, according to the TWA measuring electrocardiograph, TWA measuring method, and TWA measurement system in Embodiment 1, the use of a transformation coefficient enables a Frank's vector electrocardiogram to be synthesized from a 12-lead electrocardiogram. Therefore, the measuring person may attach the measurement electrodes to the same positions as those in the case where a 12-lead electrocardiogram is to be acquired.

Since the presence of TWA can be measured from the synthesized 12-lead electrocardiogram, the presence of TWA can be measured in the same manner as the case where a 12-lead electrocardiogram is to be acquired. Moreover, the personal coefficient specific to the patient is used for measuring the presence of TWA of the patient, and therefore an optimum result of the TWA measurement can be acquired, so that the measurement accuracy can be improved.

Embodiment 1 in which the personal coefficient is stored for each patient and in time series has been described. In the case where the storage capacity of the TWA measuring electrocardiograph is small, the personal coefficient may not be stored in time series, but only the latest personal coefficient may be updatingly stored.

Embodiment 1 is configured so that, in the case where the personal coefficient of a specific patient exists, even when the personal coefficient was produced, for example, two or three years ago, the personal coefficient can be used. In order that the presence of TWA of the patient can be examined highly accurately, however, it is preferable that a result of the TWA measurement is produced by using a personal coefficient which is acquired at a timing as close as possible to the present timing.

Alternatively, therefore, an available period (for example, one year from acquisition) of a personal coefficient may be set. In the case where the available period is expired, acquisition of the personal coefficient may be prompted in a similar manner as the case where the personal coefficient does not exist, and a process such as that shown in the flowchart of FIG. 20 may be performed.

In Embodiment 1, the transformation of the individual ID is performed in order to search and acquire the personal coefficient between hospitals. The transformation of the individual ID is performed in accordance with the specific ID. Various techniques for ID transformation are known. The technique for ID transformation is not limited to that exemplified in Embodiment 1, and any one of the various known techniques may be employed. For example, an open software application called OpenPIXPDQ is known as a software application for ID transformation between hospitals. The transformation of the ID may be performed by using such an open software application.

Embodiment 2

Next, Embodiment 2 will be described. In Embodiment 1, a Frank's vector electrocardiogram is synthesized, a vector magnitude is calculated from the synthesized Frank's vector electrocardiogram, and the presence of TWA is measured from the calculated vector magnitude. In Embodiment 2, by contrast, a vector magnitude is calculated from a Frank's vector electrocardiogram which is directly obtained from electrocardiographic signals of the measurement electrodes, and the presence of TWA is measured from the calculated vector magnitude. In Embodiment 2, the measurement of the presence of TWA is performed by using a unique technique. Therefore, the presence of TWA can be measured with an accuracy which is remarkably different from the measurement accuracy of the related art.

Hereinafter, a TWA measuring electrocardiograph and TWA measuring method of Embodiment 2 will be described.

(Configuration of TWA Measuring Electrocardiograph)

Figure 24:
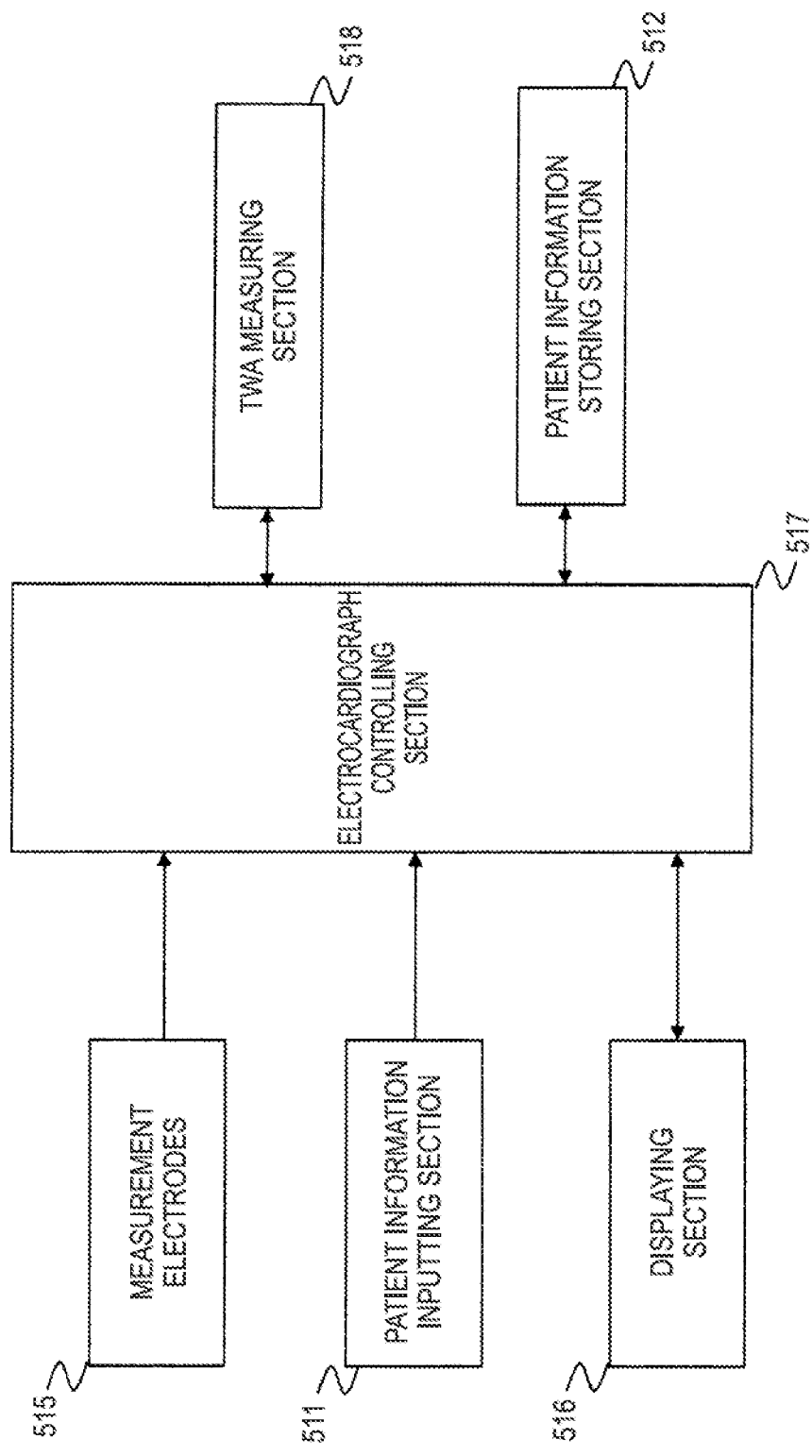
FIG. 24 is a block diagram of a TWA measuring electrocardiograph of Embodiment 2.

First, the configuration of the TWA measuring electrocardiograph of Embodiment 2 will be described. FIG. 24 is a block diagram of the TWA measuring electrocardiograph of Embodiment 2.

The TWA measuring electrocardiograph 510 includes a patient information inputting section 511, a patient information storing section 512, measurement electrodes 515, a displaying section 516, an electrocardiograph controlling section 517, and a TWA measuring section 518.

The patient information inputting section 511 is used for inputting patient information by means of key operations of the measuring person. Specifically, the patient information contains a patient ID, the name of the patient, the age of the patient, and the sex of the patient.

The patient information storing section 512 stores the patient information which is input through the patient information inputting section 511. For example, the specific ID "C123" of the patient, the name of the patient, the age of the patient, and the sex of the patient are stored as the patient ID.

The measurement electrodes 515 are electrodes which are to be attached to the body surface of the patient. The measurement electrodes 515 are attached to specific positions of the patient which are predetermined for producing a Frank's vector electrocardiogram.

The displaying section 516 displays the patient information which is input through the patient information inputting section 511, and a measurement result of the presence of TWA which is measured by the TWA measuring section 518, on a display device, or prints out them.

The electrocardiograph controlling section 517 produces a Frank's vector electrocardiogram from electrocardiographic signals of the measurement electrodes 515, and calculates a vector magnitude. The electrocardiograph controlling section 517 produces a Frank's vector electrocardiogram, and generally controls all operations of the TWA measuring electrocardiograph 510. The electrocardiograph controlling section 517 includes programs for realizing the all operations of the TWA measuring electrocardiograph 510. The operation of the electrocardiograph controlling section 517 will be described later in detail.

The TWA measuring section 518 measures the presence of TWA from the vector magnitude which is calculated by the electrocardiograph controlling section 517. In the measurement of the presence of TWA, the TWA measuring section 518 selects waveforms which can contribute to the measurement of the presence of TWA, from a plurality waveforms of the vector magnitude calculated by the electrocardiograph controlling section 517, and measures the presence of TWA from the selected waveforms. This is because, when waveforms which can contribute to the measurement of the presence of TWA are selected, the accuracy of the measurement of TWA is improved. The operation of the TWA measuring section 518 will be described later in detail.

(Operation of TWA Measuring Electrocardiograph)

Next, the operation of the TWA measuring electrocardiograph of Embodiment 2 will be described with reference to the operation flowchart of FIG. 25.

Figure 25:
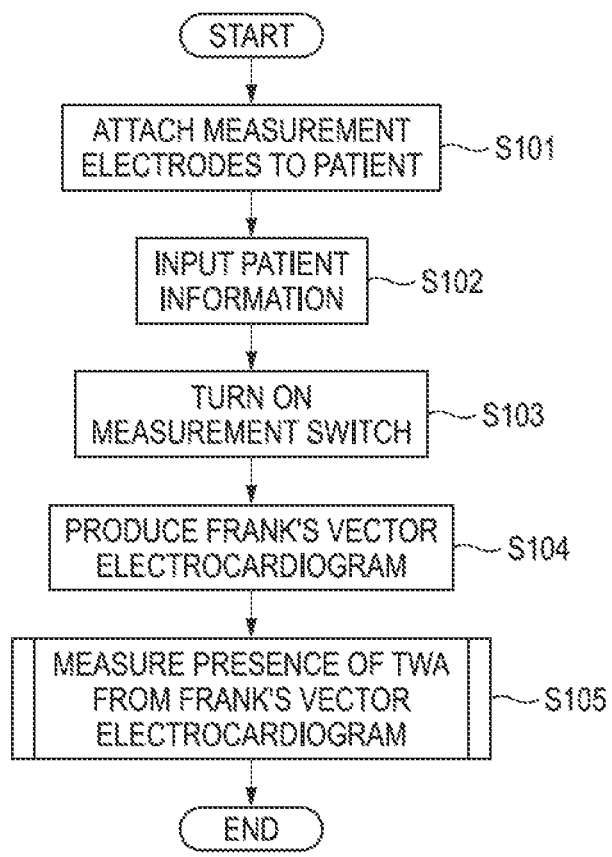
FIG. 25 is an operation flowchart of the TWA measuring electrocardiograph of Embodiment 2.

In the operation flowchart of FIG. 25, the operations of steps S101 to S103 are performed by the operator (measuring person) of the TWA measuring electrocardiograph, and the operation of step S104 is performed by the electrocardiograph controlling section 517. The operations of steps S101 to S105 correspond also to the procedure of the TWA measuring method of Embodiment 2. The operation of step S105 is performed by the TWA measuring section 518.

<Step S101>

In order to produce a Frank's vector electrocardiogram, the operator of the TWA measuring electrocardiograph 510 shown in FIG. 24 attaches the measurement electrodes 515 to predetermined portions of the body surface of the patient. Since the TWA measuring electrocardiograph 510 of Embodiment 2 targets a Frank's vector electrocardiogram, the measurement electrodes 515 are attached respectively to measurement portions of the patient which are determined for acquiring a Frank's vector electrocardiogram.

<Step S102>

Next, the operator inputs patient information through the patient information inputting section 511. For example, the specific ID "C123" and individual ID "A123" are input as the patient ID, and then the name of the patient, the age of the patient, and the sex of the patient are input.

<Step S103>

Then, the operator turns ON a measurement switch (not shown) of the TWA measuring electrocardiograph 510. When the measurement switch is turned ON, the measurement of the presence of TWA is started.

<Step S104>

The electrocardiograph controlling section 517 produces a Frank's vector electrocardiogram from electrocardiographic signals of the measurement electrodes 515 which are attached in step S101 to the patient.

<Step S105>

The electrocardiograph controlling section 517 calculates a vector magnitude from the Frank's vector electrocardiogram which is produced in step S104. The TWA measuring section 518 measures the presence of TWA from the waveform of the vector magnitude. The process of measuring the presence of TWA will be specifically described with reference to the flowchart of FIG. 26.

As described above, in the technique based on spectral analysis which is disclosed in U.S. Pat. No. 4,802,491, vector magnitude waveforms for 128 consecutive beats in which the HR is equal to or smaller than 110 during a period when a burden is applied to the subject are required.

When the waveforms are affected by noises or the conditions of HR=110 or less are not satisfied, therefore, the beat counting is not started. Considering that the time period between the ST and the T is changed depending on the HR, it is desirable to keep the HR constant as far as possible. In practice, however, the HR is hardly kept constant. Even in the case where the HR can be kept constant, an abnormal value may be included in the 128 beats.

Also in Embodiment 2, in order to eliminate such a trouble in the technique based on spectral analysis, first, waveforms of 128 or more beats, for example, 150 beats in which the HR is from 105 to 110 are selected from beats in a fixed zone. Basically, the selected 150 beats are consecutive. In the case where the beats are not consecutive, the selection is performed so as to maintain the alternation. For example, the selection in which the alternation is maintained is performed by setting the number of the unselected beats which are sandwiched between selected beats, to be even, or using, for example, the shape similarity of selected beats.

When vector magnitude waveforms for 150 beats are extracted by such a technique, the necessity of keeping the HR constant during the burdening is eliminated, and therefore the presence of TWA can be easily measured.

Next, waveforms for 128 beats in which correlations between the waveforms are equal to or larger than a predetermined threshold are selected from the selected vector magnitude waveforms for 150 beats.

In the case where an abnormal value (outlier) is included in the vector magnitude waveforms for 128 beats, moreover, the abnormal value is corrected by using another value.

As a result of such a process, the influence of an abnormal value (outlier) can be reduced as far as possible, and the accuracy of the measurement of the presence of TWA which is finally obtained is improved.

Figure 26:
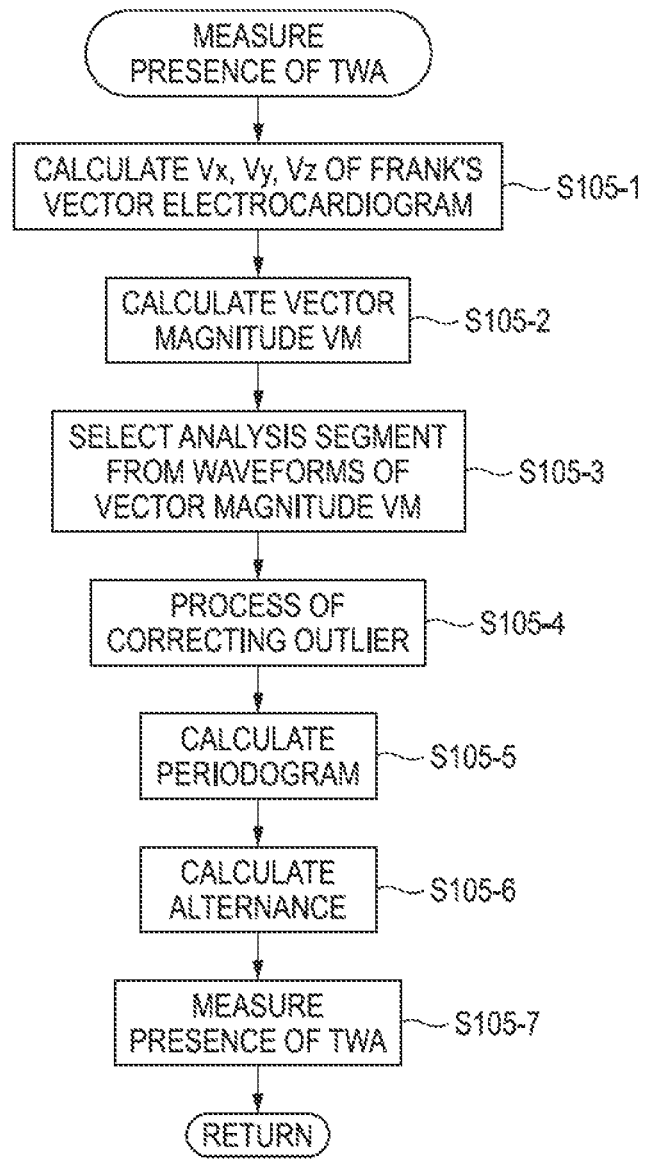
FIG. 26 is a flowchart showing procedures for measuring the presence of TWA in the TWA measuring electrocardiograph of Embodiment 2.

The operation flowchart of FIG. 26 shows the procedure for measuring the presence of TWA. The flowchart is a subroutine flowchart of step S105 in FIG. 25.

<Step S105-1>

Figure 27:
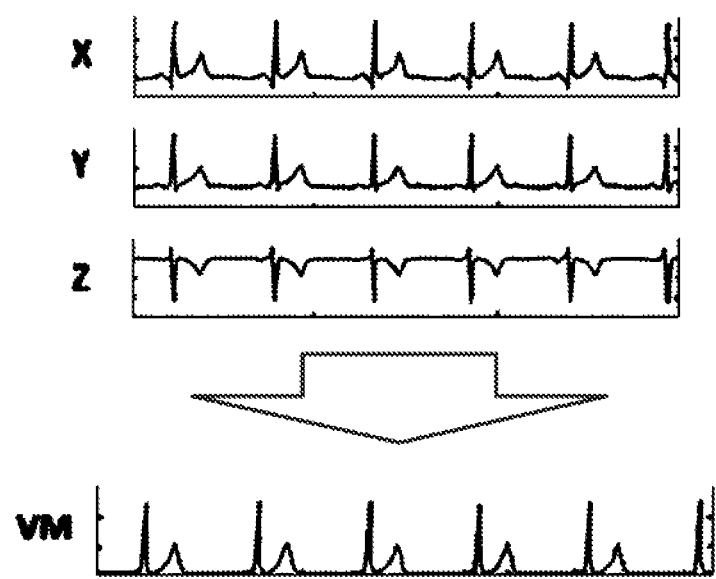
FIG. 27 shows waveform charts illustrating the process of the operation flowchart of FIG. 26.

The electrocardiograph controlling section 517 calculates lead $V_X$, lead $V_Y$, and lead $V_Z$ of the Frank's vector electrocardiogram such as shown in the upper figure of FIG. 27, from electrocardiographic signals of the measurement electrodes 515 attached to the patient.

<Step S105-2>

Then, the electrocardiograph controlling section 517 squares the values of the calculated lead $V_X$, lead $V_Y$, and lead $V_Z$, adds together the squared values, and calculates the square root of the sum of the squared values, thereby calculating the value of a vector magnitude VM such as shown in the lower figure of FIG. 27.

<Step S105-3>

The TWA measuring section 518 acquires the electrocardiogram waveform of the vector magnitude VM of the Frank's vector electrocardiogram which is obtained as described above, from the electrocardiograph controlling section 517. In order to improve the accuracy of the measurement of the presence of TWA, the TWA measuring section 518 eliminates an abnormal value and the like from the acquired electrocardiogram waveform of the vector magnitude VM, and selects waveforms which are used in the measurement of the presence of TWA.

First, the TWA measuring section 518 selects waveforms for 128 or more beats, for example, 150 beats.

In the selection of waveforms for 150 beats, as shown in FIG. 7, only beats in which the HR is from 105 to 110, and in which TWA seems to be easily produced are selected from the vector magnitude VM acquired from the electrocardiograph controlling section 517. It is preferable to select consecutive beats. In the case of consecutive 150 beats, however, there is a possibility that also noisy beats in which the presence of TWA is hardly measured may exist. This influences the measurement accuracy. Therefore, 150 beats in which TWA seems to be easily produced are inconsecutively selected.

There is a possibility that, in the thus selected vector magnitude waveforms for 150 beats, waveforms which are largely different in shape may be included. Next, therefore, the waveforms for 128 beats in which correlations between the waveforms are equal to or larger than a given threshold are selected from the vector magnitude waveforms for 150 beats.

Specifically, first, an average waveform which is obtained by averaging the vector magnitude waveforms for 150 beats in a first designated time period is acquired. Then, waveforms for 128 beats in which the correlations between the respective waveforms and the average waveform are equal to or larger than the given threshold are determined.

Then, ST-T segments of the thus selected vector magnitude waveforms for 128 beats are selected as an analysis segment.

<Step S105-4>

In the case where an outlier (abnormal value) is included in the analysis segment for 128 beats, the TWA measuring section 518 performs a process of correcting the outlier.

Outliers which seems to adversely affect the measurement of the presence of TWA are detected while being grouped into odd and even beats, and correction is performed on the detected beats.

Specifically, the intermediate value of the electrocardiogram waveforms is obtained for odd and even beats, and the standard deviation is obtained for odd and even beats. A threshold in which the standard deviation is used as a parameter, and which is used for determining an outlier is calculated, the magnitude relationship with respect to the threshold is determined, and an outlier is determined. The value which is determined as an outlier is substituted in a correction function in which the standard deviation is used as a parameter, and a correction value is calculated. Various methods of determining such a threshold, and correction functions are known. In the embodiment, any known method or function may be used.

In the waveform of the original signal which has not yet undergone the correcting process, as shown in the upper waveform chart of FIG. 8, a portion which largely drops in level exists in a middle portion. By contrast, in the waveform of the corrected signal which has undergone the correcting process, as shown in the lower waveform chart of FIG. 8, such a portion which largely drops in level does not exist in a middle portion. It is seen that the process of correcting an outlier achieves a significant effect.

<Step S105-5>

After the outlier correction, as shown in FIG. 6, the TWA measuring section 518 performs the FFT process on the analysis segment for 128 beats, and calculates a periodogram.

FIGS. 9 and 10 are views for illustrating a periodogram. The upper waveform charts of FIGS. 9 and 10 show average waveforms of odd and even beats, respectively. The lower waveform charts of FIGS. 9 and 10 show waveforms which are obtained after a periodogram is calculated.

The waveform of FIG. 9 which is obtained after a periodogram is calculated shows that, when the frequency (cycle/beat) is 0.5, the value of the vector magnitude is small. This means that there is no TWA. By contrast, the waveform of FIG. 10 which is obtained after a periodogram is calculated shows that, when the frequency (cycle/beat) is 0.5, the value of the vector magnitude is large. This means that the value of TWA is large, and the possibility that TWA exists is large.

As described above, when a periodogram is calculated, the presence of TWA can be predicted to some extent from the magnitude of the value of the vector magnitude.

<Step S105-6>

Next, the TWA measuring section 518 calculates alternance. In the waveform charts which are shown in FIGS. 9 and 10, and which are obtained after a periodogram is calculated, the zone where the cycle/beat frequency is from 0.44 to 0.49 is defined as a noise band, and the average $S_{NB}$ and standard deviation $\sigma_{NB}$ of the zone are obtained. The value which is obtained when the cycle/beat frequency is 0.5 is indicated by $S_{0.5}$, and the following Formula 4 is calculated, thereby calculating alternance $V_{alt}$.

$$V_{alt} = (S_{0.5} - S_{NB})^{1/2} \quad \text{Formula 4}$$

<Step S105-7>

The TWA measuring section 518 determines the presence of TWA. By using the average $S_{NB}$ of the zone and value of alternance $V_{alt}$ which are calculated in step S105-6, the following Formula 5 is calculated, thereby calculating an alternance ratio k.

$$k = (V_{alt})^2 / \sigma_{NB} \quad \text{Formula 5}$$

Then, the presence of TWA is determined from the values of the alternance $V_{alt}$ and the alternance ratio k. Conditions for determining the presence of TWA are the alternance $V_{alt} > 1.9\,\mu V$ and the alternance ratio k>3. When the determination conditions are satisfied, it is determined that TWA exists.

As described above, when the waveform shape of a Frank's vector electrocardiogram is analyzed, it is possible to determine the presence of TWA in which T waves having different shapes appear alternately at each beat (ABABAB . . . ).

According to Embodiment 2, as described above, the presence of TWA can be accurately measured from a Frank's vector electrocardiogram which is currently used.

Alternatively, the displaying section 516 may comparatively displays a measurement result obtained by the related-art technique in which the presence of TWA is acquired from a Frank's vector electrocardiogram, and that obtained by the technique in which the presence of TWA is acquired according to Embodiment 2.

Embodiment 3

Next, Embodiment 3 will be described. In Embodiment 2, a vector magnitude is calculated from a Frank's vector electrocardiogram which is directly obtained from electrocardiographic signals of the measurement electrodes, and the presence of TWA is measured from the calculated vector magnitude. In Embodiment 3, by contrast, the presence of TWA is measured from a scalar electrocardiogram which is synthesized or directly produced from electrocardiographic signals of the measurement electrodes. Therefore, the presence of TWA can be measured from a scalar electrocardiogram although such a measurement cannot be performed in the related art. Examples of a scalar electrocardiogram are a 12-lead electrocardiogram, a Holter electrocardiogram, an event electrocardiogram, an exercise electrocardiogram, and a monitoring electrocardiogram. In Embodiment 3, the presence of TWA can be measured from any one of electrocardiograms.

Hereinafter, a TWA measuring electrocardiograph and TWA measuring method of Embodiment 3 will be described.

(Configuration of TWA Measuring Electrocardiograph)

First, the configuration of the TWA measuring electrocardiograph of Embodiment 3 will be described. Although FIG. 24 is a block diagram of the TWA measuring electrocardiograph of Embodiment 2, the apparent configuration of the TWA measuring electrocardiograph of Embodiment 3 is identical with that shown in the block diagram of the TWA measuring electrocardiograph of Embodiment 2.

The TWA measuring electrocardiograph 510 includes a patient information inputting section 511, a patient information storing section 512, measurement electrodes 515, a displaying section 516, an electrocardiograph controlling section 517, and a TWA measuring section 518.

The patient information inputting section 511 is used for inputting patient information by means of key operations of the measuring person. Specifically, the patient information contains a patient ID, the name of the patient, the age of the patient, and the sex of the patient.

The patient information storing section 512 stores the patient information which is input through the patient information inputting section 511. For example, the specific ID "C123" of the patient, the name of the patient, the age of the patient, and the sex of the patient are stored as the patient ID.

The measurement electrodes 515 are electrodes which are to be attached to the body surface of the patient. The measurement electrodes 515 are attached to specific positions of the patient which are predetermined for producing a scalar electrocardiogram.

The displaying section 516 displays the patient information which is input through the patient information inputting section 511, and a measurement result of the presence of TWA which is measured by the TWA measuring section 518, on a display device, or prints out them.

The electrocardiograph controlling section 517 produces a scalar electrocardiogram from electrocardiographic signals of the measurement electrodes 515. The electrocardiograph controlling section 517 produces a scalar electrocardiogram, and generally controls all operations of the TWA measuring electrocardiograph 510. The electrocardiograph controlling section 517 includes programs for realizing the all operations of the TWA measuring electrocardiograph 510. The operation of the electrocardiograph controlling section 517 will be described later in detail.

The TWA measuring section 518 measures the presence of TWA from the scalar electrocardiogram which is produced by the electrocardiograph controlling section 517. In the measurement of the presence of TWA, the TWA measuring section 518 selects waveforms which can contribute to the measurement of the presence of TWA, from a plurality waveforms of the scalar electrocardiogram produced by the electrocardiograph controlling section 517, and measures the presence of TWA from the selected waveforms. This is because, when waveforms which can contribute to the measurement of the presence of TWA are selected, the accuracy of the measurement of TWA is improved. The operation of the TWA measuring section 518 will be described later in detail.

(Operation of TWA Measuring Electrocardiograph)

Next, the operation of the TWA measuring electrocardiograph of Embodiment 3 will be described with reference to the operation flowchart of FIG. 28.

Figure 28:
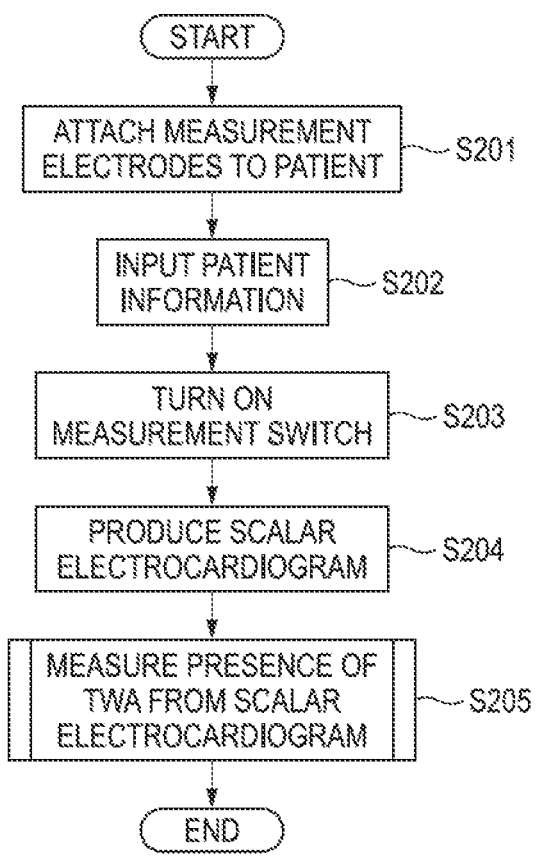
FIG. 28 is a flowchart of a TWA measuring electrocardiograph of Embodiment 3.

In the operation flowchart of FIG. 28, the operations of steps S201 to S203 are performed by the operator (measuring person) of the TWA measuring electrocardiograph, and the operation of step S204 is performed by the electrocardiograph controlling section 517. The operations of steps S201 to S205 correspond also to the procedure of the TWA measuring method of Embodiment 2. The operation of step S205 is performed by the TWA measuring section 518.

<Step S201>

In order to calculate a scalar electrocardiogram, the operator of the TWA measuring electrocardiograph 510 shown in FIG. 24 attaches the measurement electrodes 515 to predetermined portions of the body surface of the patient. In the case where a 12-lead electrocardiogram is employed as a scalar electrocardiogram, for example, the measurement electrodes are attached respectively to measurement portions of the patient which are determined for measuring a 12-lead electrocardiogram. In the case where a Holter electrocardiogram, an event electrocardiogram, an exercise electrocardiogram, or a monitoring electrocardiogram is employed, the measurement electrodes are attached respectively to measurement portions of the patient which are determined for measuring the electrocardiogram.

<Step S202>

Next, the operator inputs patient information through the patient information inputting section 511. For example, the specific ID "C123" and individual ID "A123" are input as the patient ID, and then the name of the patient, the age of the patient, and the sex of the patient are input.

<Step S203>

Then, the operator turns ON a measurement switch (not shown) of the TWA measuring electrocardiograph 510. When the measurement switch is turned ON, the measurement of the presence of TWA is started.

<Step S204>

The electrocardiograph controlling section 517 produces a scalar electrocardiogram from electrocardiographic signals of the measurement electrodes 515 which are attached in step S201 to the patient.

<Step S205>

The TWA measuring section 518 measures the presence of TWA from the waveform of the scalar electrocardiogram produced in step S204. The process of measuring the presence of TWA will be specifically described with reference to the flowchart of FIG. 29.

As described above, in the technique based on spectral analysis which is disclosed in U.S. Pat. No. 4,802,491, vector magnitude waveforms for 128 consecutive beats in which the HR is equal to or smaller than 110 during a period when a burden is applied to the subject are required.

When the waveforms are affected by noises or the conditions of HR=110 or less are not satisfied, therefore, the beat counting is not started. Considering that the time period between the ST and the T is changed depending on the HR, it is desirable to keep the HR constant as far as possible. In practice, however, the HR is hardly kept constant. Even in the case where the HR can be kept constant, an abnormal value may be included in the 128 beats.

Also in Embodiment 3, in order to eliminate such a trouble in the technique based on spectral analysis, first, waveforms of 128 or more beats, for example, 150 beats in which the HR is from 105 to 110 are selected from beats in a fixed zone. Basically, the selected 150 beats are consecutive. In the case where the beats are not consecutive, the selection is performed so as to maintain the alternation. For example, the selection in which the alternation is maintained is performed by setting the number of the unselected beats which are sandwiched between selected beats, to be even, or using, for example, the shape similarity of selected beats.

When scalar electrocardiogram waveforms for 150 beats are extracted by such a technique, the necessity of keeping the HR constant during the burdening is eliminated, and therefore the presence of TWA can be easily measured.

Next, waveforms for 128 beats in which correlations between the waveforms are equal to or larger than a predetermined threshold are selected from the selected scalar electrocardiogram waveforms for 150 beats.

In the case where an abnormal value (outlier) is included in the scalar electrocardiogram waveforms for 128 beats, moreover, the abnormal value is corrected by using another value.

As a result of such a process, the influence of an abnormal value (outlier) can be reduced as far as possible, and the accuracy of the measurement of the presence of TWA which is finally obtained is improved.

Figure 29:
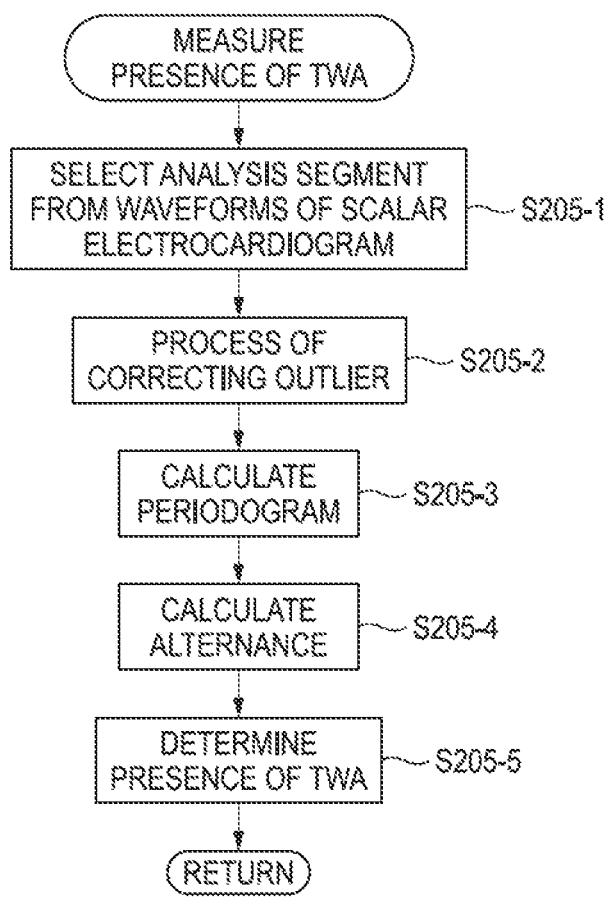
FIG. 29 is a flowchart showing procedures for measuring the presence of TWA in the TWA measuring electrocardiograph of Embodiment 3.

The operation flowchart of FIG. 29 shows the procedure for measuring the presence of TWA. The flowchart is a subroutine flowchart of step S205 in FIG. 28.

<Step S205-1>

The electrocardiograph controlling section 517 produces a scalar electrocardiogram which is usually obtained from the measurement electrodes 515, from electrocardiographic signals of the measurement electrodes 515 attached to the patient. The TWA measuring section 518 acquires the thus produced scalar electrocardiogram waveform from the electrocardiograph controlling section 517. In order to improve the accuracy of the measurement of the presence of TWA, the TWA measuring section 518 eliminates an abnormal value and the like from the acquired scalar electrocardiogram waveform, and selects waveforms which are used in the measurement of the presence of TWA.

First, the TWA measuring section 518 selects waveforms for 128 or more beats, for example, 150 beats. In the selection of waveforms for 150 beats, as shown in FIG. 7, only beats in which the HR is from 105 to 110, and in which TWA seems to be easily produced are selected from the scalar electrocardiogram waveform acquired from the electrocardiograph controlling section 517. It is preferable to select consecutive beats. In the case of consecutive 150 beats, however, there is a possibility that also noisy beats in which the presence of TWA is hardly measured may exist. This influences the measurement accuracy. Therefore, 150 beats in which TWA seems to be easily produced are inconsecutively selected.

There is a possibility that, in the thus selected scalar electrocardiogram waveforms for 150 beats, waveforms which are largely different in shape may be included. Next, therefore, the waveforms for 128 beats in which correlations between the waveforms are equal to or larger than a given threshold are selected from the waveforms for 150 beats.

Specifically, first, an average waveform which is obtained by averaging the waveforms for 150 beats in a first designated time period is acquired. Then, waveforms for 128 beats in which the correlations between the respective waveforms and the average waveform are equal to or larger than the given threshold are determined.

Then, ST-T segments of the thus selected scalar electrocardiogram waveforms for 128 beats are selected as an analysis segment.

<Step S205-2>

In the case where an outlier (abnormal value) is included in the analysis segment for 128 beats, the TWA measuring section 518 performs a process of correcting the outlier.

Outliers which seems to adversely affect the measurement of the presence of TWA are detected while being grouped into odd and even beats, and correction is performed on the detected beats.

Specifically, the intermediate value of the electrocardiogram waveforms is obtained for odd and even beats, and the standard deviation is obtained for odd and even beats. A threshold in which the standard deviation is used as a parameter, and which is used for determining an outlier is calculated, the magnitude relationship with respect to the threshold is determined, and an outlier is determined. The value which is determined as an outlier is substituted in a correction function in which the standard deviation is used as a parameter, and a correction value is calculated. Various methods of determining such a threshold, and correction functions are known. In the embodiment, any known method or function may be used.

In the waveform of the original signal which has not yet undergone the correcting process, as shown in the upper waveform chart of FIG. 8, a portion which largely drops in level exists in a middle portion. By contrast, in the waveform of the corrected signal which has undergone the correcting process, as shown in the lower waveform chart of FIG. 8, such a portion which largely drops in level does not exist in a middle portion. It is seen that the process of correcting an outlier achieves a significant effect.

<Step S205-3>

After the outlier correction, as shown in FIG. 6, the TWA measuring section 518 performs the FFT process on the analysis segment for 128 beats, and calculates a periodogram.

FIGS. 9 and 10 are views for illustrating a periodogram. The upper waveform charts of FIGS. 9 and 10 show average waveforms of odd and even beats, respectively. The lower waveform charts of FIGS. 9 and 10 show waveforms which are obtained after a periodogram is calculated.

The waveform of FIG. 9 which is obtained after a periodogram is calculated shows that, when the frequency (cycle/beat) is 0.5, the value of the vector magnitude is small. This means that there is no TWA. By contrast, the waveform of FIG. 10 which is obtained after a periodogram is calculated shows that, when the frequency (cycle/beat) is 0.5, the value of the vector magnitude is large. This means that the value of TWA is large, and the possibility that TWA exists is large.

As described above, when a periodogram is calculated, the presence of TWA can be predicted to some extent from the magnitude of the value of the vector magnitude.

<Step S205-4>

Next, the TWA measuring section 518 calculates alternance. In the waveform charts which are shown in FIGS. 9 and 10, and which are obtained after a periodogram is calculated, the zone where the cycle/beat frequency is from 0.44 to 0.49 is defined as a noise band, and the average $S_{NB}$ and standard deviation $\sigma_{NB}$ of the zone are obtained. The value which is obtained when the cycle/beat frequency is 0.5 is indicated by $S_{0.5}$, and the following Formula 4 is calculated, thereby calculating alternance $V_{alt}$.

$$V_{alt} = (S_{0.5} - S_{NB})^{1/2} \quad \text{Formula 4}$$

<Step S205-5>

The TWA measuring section 518 determines the presence of TWA. By using the average $S_{NB}$ of the zone and value of alternance $V_{alt}$ which are calculated in step S205-4, the following Formula 5 is calculated, thereby calculating an alternance ratio k.

$$k = (V_{alt})^2 / \sigma_{NB} \quad \text{Formula 5}$$

Then, the presence of TWA is determined from the values of the alternance $V_{alt}$ and the alternance ratio k. Conditions for determining the presence of TWA are the alternance $V_{alt} > 1.9$ μV and the alternance ratio k>3. When the determination conditions are satisfied, it is determined that TWA exists.

As described above, when the waveform shape of a scalar electrocardiogram is analyzed, it is possible to determine the presence of TWA in which T waves having different shapes appear alternately at each beat (ABABAB . . . ).

According to Embodiment 3, as described above, the presence of TWA can be accurately measured from a scalar electrocardiogram which is currently used.

According to an aspect of the presently disclosed subject matter, as described above, the presence of TWA can be accurately measured by using an electrocardiogram which is produced from any one of a Frank's vector electrocardiogram and scalar electrocardiogram that are used in the related art.

According to an aspect of the presently disclosed subject matter, the electrocardiograph controlling section can produce an electrocardiogram by using any one of various measuring methods. The number and positions of the measurement electrodes to be attached to the subject are different depending on the measuring method which is used for acquiring the electrocardiogram.

According to a Frank's vector electrocardiogram or a usual scalar electrocardiogram, i.e., a standard 12-lead electrocardiogram, a synthesized 12-lead electrocardiogram, a Holter electrocardiogram, an event electrocardiogram, an exercise electrocardiogram, or a monitoring electrocardiogram, for example, the number and positions of the measurement electrodes to be attached to the subject are different. The TWA measuring section measures the presence of TWA based on the vector magnitude or electrocardiogram which is produced by the electrocardiograph controlling section.

According to an aspect of the presently disclosed subject matter, the presence of TWA can be measured from an electrocardiogram acquired by any one of various measuring methods. Moreover, the presence of TWA can be measured without being restricted by conditions, and therefore the burden on the measuring person and the subject can be reduced.

What is claimed is:

1. A T-Wave Alternans (TWA) measuring apparatus comprising:
    an electrocardiograph controlling section which is configured to produce an electrocardiogram from electrocardiographic signals of a subject; and
    a TWA measuring section which is configured to select a plurality of consecutive waveforms from the electrocardiogram, filter waveforms corresponding to noisy heart beats of the subject from the plurality of consecutive waveforms, and measure a presence of TWA by using the filtered plurality of consecutive waveforms.

2. The TWA measuring apparatus according to claim 1, further comprising a transformation coefficient storing section which is configured to store a transformation coefficient, wherein
the electrocardiogram is a Frank's vector electrocardiogram,
the electrocardiograph controlling section is configured to synthesize the Frank's vector electrocardiogram from the electrocardiographic signals by using the transformation coefficient, and
the TWA measuring section is configured to select the plurality of consecutive waveforms from waveforms of a vector magnitude which is calculated from the Frank's vector electrocardiogram.

3. The TWA measuring apparatus according to claim 2, wherein the transformation coefficient storing section includes:
a personal coefficient database which is configured to store, as the transformation coefficient, a personal coefficient which is specific to the subject and which is acquired from the subject; and
a group coefficient database which is configured to store, as the transformation coefficient, a group coefficient which is an average of a plurality of transformation coefficients which are acquired from an unspecified number of persons of a statistically effective population in order to synthesize the Frank's vector electrocardiogram of the subject.

4. The TWA measuring apparatus according to claim 3, wherein when the personal coefficient acquired from the subject exists in the personal coefficient database, the electrocardiograph controlling section is configured to synthesize the Frank's vector electrocardiogram by using the personal coefficient as the transformation coefficient, and
when the personal coefficient does not exist in the personal coefficient database, the electrocardiograph controlling section is configured to synthesize the Frank's vector electrocardiogram by using the group coefficient existing in the group coefficient database as the transformation coefficient.

5. The TWA measuring apparatus according to claim 3, further comprising a displaying section,
wherein when the personal coefficient of the subject does not exist in the personal coefficient database, the electrocardiograph controlling section is configured to cause the displaying section to display a message for prompting acquisition of the personal coefficient.

6. The TWA measuring apparatus according to claim 3, wherein the electrocardiograph controlling section is configured to calculate the personal coefficient of the subject from the electrocardiographic signals, and store the calculated personal coefficient in the personal coefficient database.

7. The TWA measuring apparatus according to claim 1, wherein
the electrocardiogram is a Frank's vector electrocardiogram,
the electrocardiograph controlling section is configured to produce the Frank's vector electrocardiogram directly from the electrocardiographic signals, and
the TWA measuring section is configured to select the plurality of consecutive waveforms from waveforms of a vector magnitude which is calculated from the Frank's vector electrocardiogram.

8. The TWA measuring apparatus according to claim 1, wherein
the electrocardiogram is a scalar electrocardiogram,
the electrocardiograph controlling section is configured to synthesize or directly produce the scalar electrocardiogram from the electrocardiographic signals, and
the TWA measuring section is configured to select the plurality of consecutive waveforms from waveforms of the scalar electrocardiogram.

9. The TWA measuring apparatus according to claim 8, wherein the scalar electrocardiogram is one of a 12-lead electrocardiogram, a Holter electrocardiogram, an event electrocardiogram, an exercise electrocardiogram, and a monitoring electrocardiogram.

10. The TWA measuring apparatus according to claim 1, wherein the TWA measuring section is configured to select the plurality of consecutive waveforms from waveforms of a plurality of heart beats.

11. The TWA measuring apparatus according to claim 10, wherein in a case where an abnormal value is included in the filtered plurality of consecutive waveforms, the TWA measuring section is configured to correct the abnormal value.

12. A TWA measuring method comprising:
producing an electrocardiogram from electrocardiographic signals of a subject;
selecting a plurality of consecutive waveforms from the electrocardiogram;
filtering waveforms corresponding to noisy heart beats of the subject from the plurality of consecutive waveforms; and
measuring a presence of TWA by using the filtered plurality of consecutive waveforms.

13. The TWA measuring method according to claim 12, wherein
the electrocardiogram is a Frank's vector electrocardiogram,
the producing comprises synthesizing the Frank's vector electrocardiogram from the electrocardiographic signals by using a transformation coefficient, and
the selecting comprises selecting the plurality of consecutive waveforms from waveforms of a vector magnitude which is calculated from the Frank's vector electrocardiogram.

14. The TWA measuring method according to claim 12, wherein
the electrocardiogram is a Frank's vector electrocardiogram,
the producing comprises producing the Frank's vector electrocardiogram directly from the electrocardiographic signals, and
the selecting comprises selecting the plurality of consecutive waveforms from waveforms of a vector magnitude which is calculated from the Frank's vector electrocardiogram.

15. The TWA measuring method according to claim 12, wherein,
the electrocardiogram is a scalar electrocardiogram,
the producing comprises synthesizing the scalar electrocardiogram or producing the scalar electrocardiogram directly from the electrocardiographic signals, and
the selecting comprises selecting the plurality of consecutive waveforms from waveforms of the scalar electrocardiogram.

16. The TWA measuring method according to claim 15, wherein the scalar electrocardiogram is one of a 12-lead electrocardiogram, a Holter electrocardiogram, an event electrocardiogram, an exercise electrocardiogram, and a monitoring electrocardiogram.

17. The TWA measuring method according to claim 12, wherein the selecting comprises selecting the plurality of consecutive waveforms from waveforms of a plurality of heart beats.

18. The TWA measuring method according to claim 17, further comprising:
- in a case where an abnormal value is included in the filtered plurality of consecutive waveforms, correcting the abnormal value.

\* \* \* \* \*